US012806346B2

(12) United States Patent
Warren et al.

(10) Patent No.: US 12,806,346 B2
(45) Date of Patent: Nov. 24, 2026

(54) NEBULIZER APPARATUS AND METHODS OF USING NEBULIZER APPARATUS

(71) Applicant: Pneumoflex Systems, LLC, Melbourne, FL (US)

(72) Inventors: Johnathen Warren, Melbourne, FL (US); Stuart P. Miller, Indialantic, FL (US); W. Robert Addington, Melbourne Beach, FL (US); Robert E. Stephens, Parkville, MO (US)

(73) Assignee: Pneumoflex Systems, LLC, Melbourne, FL (US)

( * ) Notice: Subject to any disclaimer, the term of this patent is extended or adjusted under 35 U.S.C. 154(b) by 603 days.

(21) Appl. No.: 18/455,919

(22) Filed: Aug. 25, 2023

(65) Prior Publication Data

US 2024/0066240 A1 Feb. 29, 2024

Related U.S. Application Data

(60) Provisional application No. 63/373,986, filed on Aug. 30, 2022.

(51) Int. Cl.
*A61M 11/00* (2006.01)

(52) U.S. Cl.
CPC ... *A61M 11/003* (2014.02); *A61M 2205/3368* (2013.01)

(58) Field of Classification Search
CPC ................ A61M 11/02; A61M 11/002; A61M 2205/8225; A61M 16/14; A61M 15/002;
(Continued)

(56) References Cited

U.S. PATENT DOCUMENTS 5,503,139 A 4/1996 McMahon et al.
7,712,466 B2 5/2010 Addington et al.
(Continued)

FOREIGN PATENT DOCUMENTS

CA 3036631 A1 6/2018
EP 1370315 B1 11/2011
(Continued)

OTHER PUBLICATIONS

International Search Report and Written Opinion dated Feb. 12, 2024 for PCT/US2023/072894.
(Continued)

*Primary Examiner* — Kendra D Carter
*Assistant Examiner* — Keira Eileen Callison
(74) *Attorney, Agent, or Firm* — King & Spalding LLP

(57) ABSTRACT

A nebulizer includes a nebulizer top detachably coupled to a nebulizer bottom with a nozzle assembly that fits between the nebulizer top and nebulizer bottom. The components of the nebulizer are formed so that each be easily replaced by a counterpart component of similar design but with a different property. The nozzle assembly is configured to be replaced with a second nozzle assembly that has a different aperture size that produces a different size of aerosol droplet. Additionally, a diffuser attached to the nebulizer top or nebulizer bottom can be replaced by a second nebulizer top or nebulizer bottom with a second diffuser in a different position that produces a different size of aerosol droplet. A sensor module attached to the nebulizer measures properties associated with the performance of the nebulizer.

18 Claims, 17 Drawing Sheets

(58) Field of Classification Search
CPC ........ A61M 11/003; A61M 2205/3368; A61M 15/008; A61M 16/161; A61M 2205/3334; A61M 2205/3553; A61M 2205/3592; A61M 2230/43; A61M 11/06
USPC ............ 128/200.14, 200.22, 203.12, 200.18, 128/200.21, 200.19, 204.25
See application file for complete search history.

(56) References Cited

U.S. PATENT DOCUMENTS

| | | | |
|---|---|---|---|
| 7,726,306 | B2 | 6/2010 | Addington et al. |
| 8,333,190 | B2 | 12/2012 | Addington et al. |
| 8,671,934 | B2 | 3/2014 | Addington et al. |
| 9,022,027 | B2 | 5/2015 | Addington et al. |
| 9,227,029 | B2 | 1/2016 | Addington et al. |
| 9,452,270 | B2 | 9/2016 | Addington et al. |
| 9,452,274 | B2 | 9/2016 | Addington et al. |
| 2004/0031485 | A1 | 2/2004 | Rustad et al. |
| 2006/0219814 | A1 | 10/2006 | Benalikhoudja |
| 2007/0123793 | A1 | 5/2007 | Addington et al. |
| 2007/0137648 | A1 | 6/2007 | Addington et al. |
| 2008/0283049 | A1* | 11/2008 | Mahoney .............. A61M 15/00 128/200.14 |
| 2011/0114090 | A1 | 5/2011 | Piper |
| 2012/0190999 | A1 | 7/2012 | Addington et al. |
| 2013/0192594 | A1 | 8/2013 | Addington et al. |
| 2014/0174435 | A1 | 6/2014 | Addington |
| 2014/0261400 | A1 | 9/2014 | Addington et al. |
| 2015/0224278 | A1 | 8/2015 | Addington et al. |
| 2018/0161531 | A1* | 6/2018 | Costella ............ A61M 16/0051 |
| 2020/0330719 | A1 | 10/2020 | Segal |
| 2021/0022391 | A1 | 1/2021 | Minami et al. |

FOREIGN PATENT DOCUMENTS

| | | | | |
|---|---|---|---|---|
| WO | WO-2011058477 | A1 * | 5/2011 | ........ A61M 15/0085 |
| WO | WO-2014164175 | A2 * | 10/2014 | ......... A63B 21/0085 |
| WO | WO-2019236899 | A1 * | 12/2019 | .......... A61M 16/127 |
| WO | WO-2021038467 | A1 * | 3/2021 | ............. A63B 23/18 |

OTHER PUBLICATIONS

European Search Report for EP Application No. 23861453.1, dated Jul. 15, 2026, 14 pages.

First Examination Report for IN Application No. 202517016417, dated Jul. 27, 2026, 10 pages.

* cited by examiner

NEBULIZER APPARATUS AND METHODS OF USING NEBULIZER APPARATUS

RELATED APPLICATIONS

The present application claims the benefit of U.S. Provisional Patent Application No. 63/373,986 filed Aug. 30, 2022, the entire content of which is incorporated herein by reference.

TECHNICAL FIELD

Embodiments of the technology relate generally to a nebulizer for delivering medication to a patient's lungs.

BACKGROUND

A nebulizer is a device used to deliver medication to the lungs. The nebulizer typically uses a mechanical means, such as an air flow, a mesh, or ultrasonic means, to disperse liquid medication into an aerosol of droplets that are inhaled by the patient. While improvements have been made to nebulizers in recent years, a variety of shortcomings persist.

First, the size of the droplets of medication in the aerosol can be too large for the intended treatment. Oversized aerosol droplets have a greater tendency to be wasted by dispersion into the ambient environment before they can be inhaled by the patient. Also, certain types of medications and treatment methods can require, or be more effective with, a smaller size of droplets in the aerosol in order to reach the intended area of the lungs. If the aerosol droplets are too large, the medication may be deposited in the throat instead of reaching the lungs. When the medication droplets deposit in the throat, they also have a tendency to be wasted when the patient exhales and pushes the droplets out of the mouth and into the ambient environment.

Second, with existing nebulizers, it can be difficult to estimate the dosage of the medication being delivered to the patient and to repeatedly provide a consistent dosage to the patient. Third, the handling of medication and the potential for contamination can be challenges with existing nebulizers. Accordingly, improvements to existing nebulizers would be beneficial.

SUMMARY

One example embodiment is directed to a nebulizer comprising a nebulizer body and a nozzle assembly. The nebulizer body can comprise: a nebulizer mouthpiece, a nebulizer top, and a nebulizer bottom, wherein the nebulizer top is configured to detachably couple dot the nebulizer bottom. The nozzle assembly can comprise: a suction line having a suction line inlet, a suction line outlet, and a suction line longitudinal axis passing through the suction line inlet and the suction line outlet; a nozzle integrally joined to the suction line, the nozzle having a nozzle inlet, a nozzle outlet, and a nozzle longitudinal axis passing through the nozzle inlet and the nozzle outlet, wherein the nozzle longitudinal axis is substantially perpendicular to the suction line longitudinal axis, and wherein the nozzle assembly is configured to detachably couple to the nebulizer body between the nebulizer top and the nebulizer bottom. The nebulizer can further comprise a diffuser projecting from an inner surface of the nebulizer top or the nebulizer bottom towards the nozzle assembly, the diffuser comprising an impact surface. Lastly, at least one of the nebulizer top, the nebulizer bottom, and the nozzle assembly can be replaceable with a counterpart component having at least one different property, wherein the counterpart component is selected to produce a target droplet size for a medicine disposed in the nebulizer.

Another example embodiment comprises a method of using a nebulizer. The method can comprise: providing a nebulizer top and a nebulizer bottom; inserting a nozzle assembly between the nebulizer top and the nebulizer bottom and coupling the nebulizer top to the nebulizer bottom with the nozzle assembly located therebetween; coupling a gas supply to a nozzle inlet of the nozzle assembly; providing nebulized medicine that flows from a mouthpiece of the nebulizer; collecting, with a sensor of a sensor module coupled to the nebulizer, data associated with operation of the nebulizer; and providing the data to a processor that analyzes the data and generates a report associated with the operation of the nebulizer.

The foregoing embodiments are non-limiting examples and other aspects and embodiments will be described herein. The foregoing summary is provided to introduce various concepts in a simplified form that are further described below in the detailed description. This summary is not intended to identify required or essential features of the claimed subject matter nor is the summary intended to limit the scope of the claimed subject matter.

BRIEF DESCRIPTION OF THE DRAWINGS

The accompanying drawings illustrate only example embodiments of nebulizer apparatus and methods of using a nebulizer. Therefore, the examples provided are not to be considered limiting of the scope of this disclosure. The principles illustrated in the example embodiments of the drawings can be applied to alternate methods and apparatus. Additionally, the elements and features shown in the drawings are not necessarily to scale, emphasis instead being placed upon clearly illustrating the principles of the example embodiments. Certain dimensions or positions may be exaggerated to help visually convey such principles. In the drawings, the same reference numerals used in different embodiments designate like or corresponding, but not necessarily identical, elements.

DETAILED DESCRIPTION OF EXAMPLE EMBODIMENTS

The example embodiments discussed herein are directed to nebulizer apparatus and methods of using nebulizer apparatus. As explained above, nebulizers can have various shortcomings. Improvements to nebulizers are described in commonly owned U.S. Pat. Nos. 9,227,029 and 9,452,270, the contents of which are incorporated herein by reference. However, the example embodiments described herein provide further improvements to existing nebulizers. First, the example nebulizers disclosed herein allow for easily interchanging components of the nebulizer to provide greater control over the size of the droplets in the aerosol the nebulizer generates. Greater control of the aerosol droplet size allows for more effective administration of the medication to the patient. A second advantage of the disclosed nebulizer embodiments is that greater control of the aerosol droplet size results in more efficient use of the medication because less of the medication is wasted. The example nebulizer apparatus described herein also can include one or more sensors providing additional advantages as will be described further below. The nebulizer embodiments described herein can be implemented as an intra-oral nebulizer, a metered dose nebulizer, or a ventilator nebulizer.

While example embodiments of nebulizer apparatus and methods of using nebulizer apparatus are provided in the descriptions that follow, it should be understood that modifications to the embodiments described herein are within the scope of this disclosure. In the following paragraphs, particular embodiments will be described in further detail by way of example with reference to the drawings. In the description, well-known components, methods, and/or processing techniques are omitted or briefly described. Furthermore, reference to various feature(s) of the embodiments is not to suggest that all embodiments must include the referenced feature(s).

Figure 1:
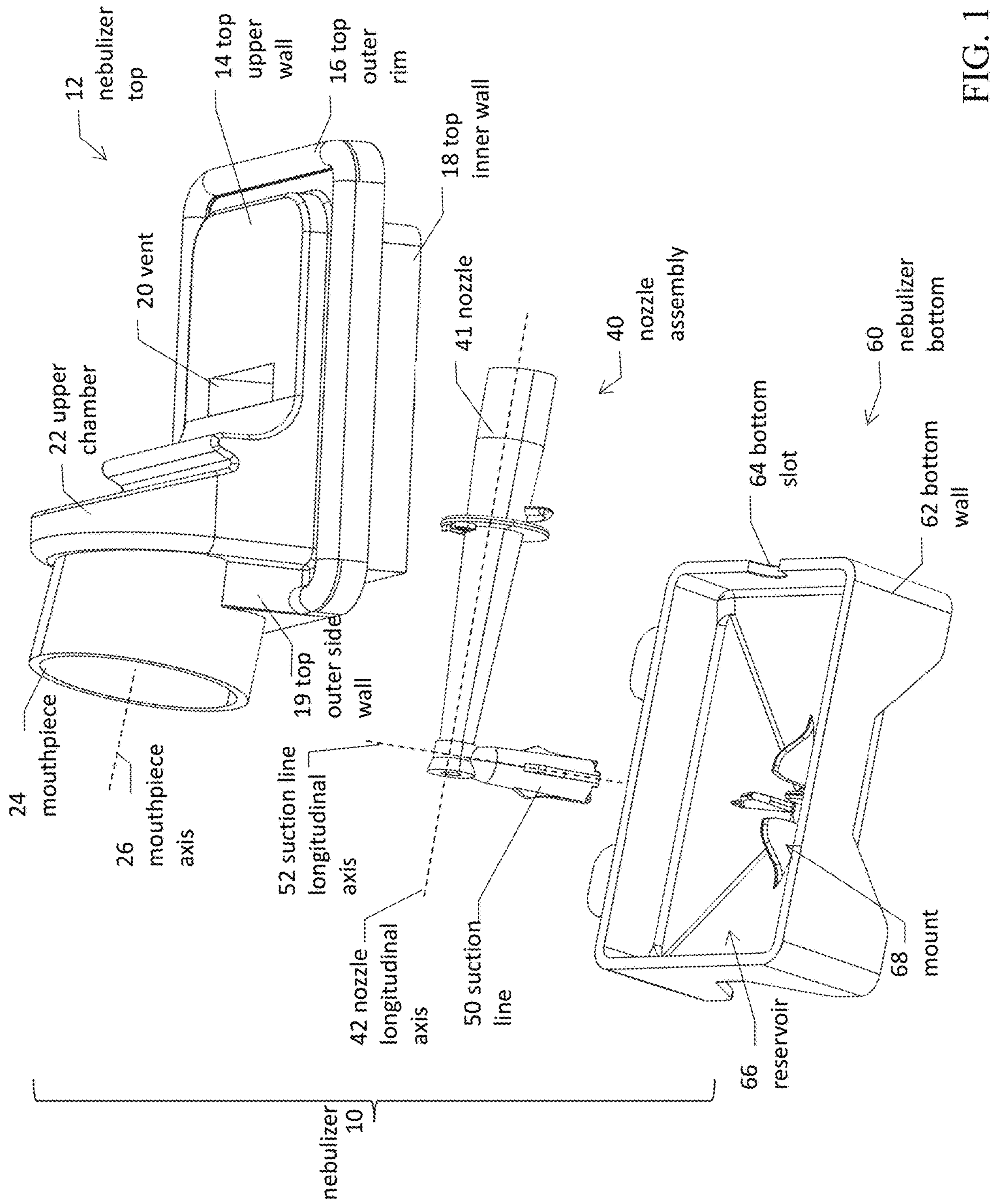
FIG. 1 illustrates a nebulizer in accordance with an example embodiment of the disclosure.
Figure 2:
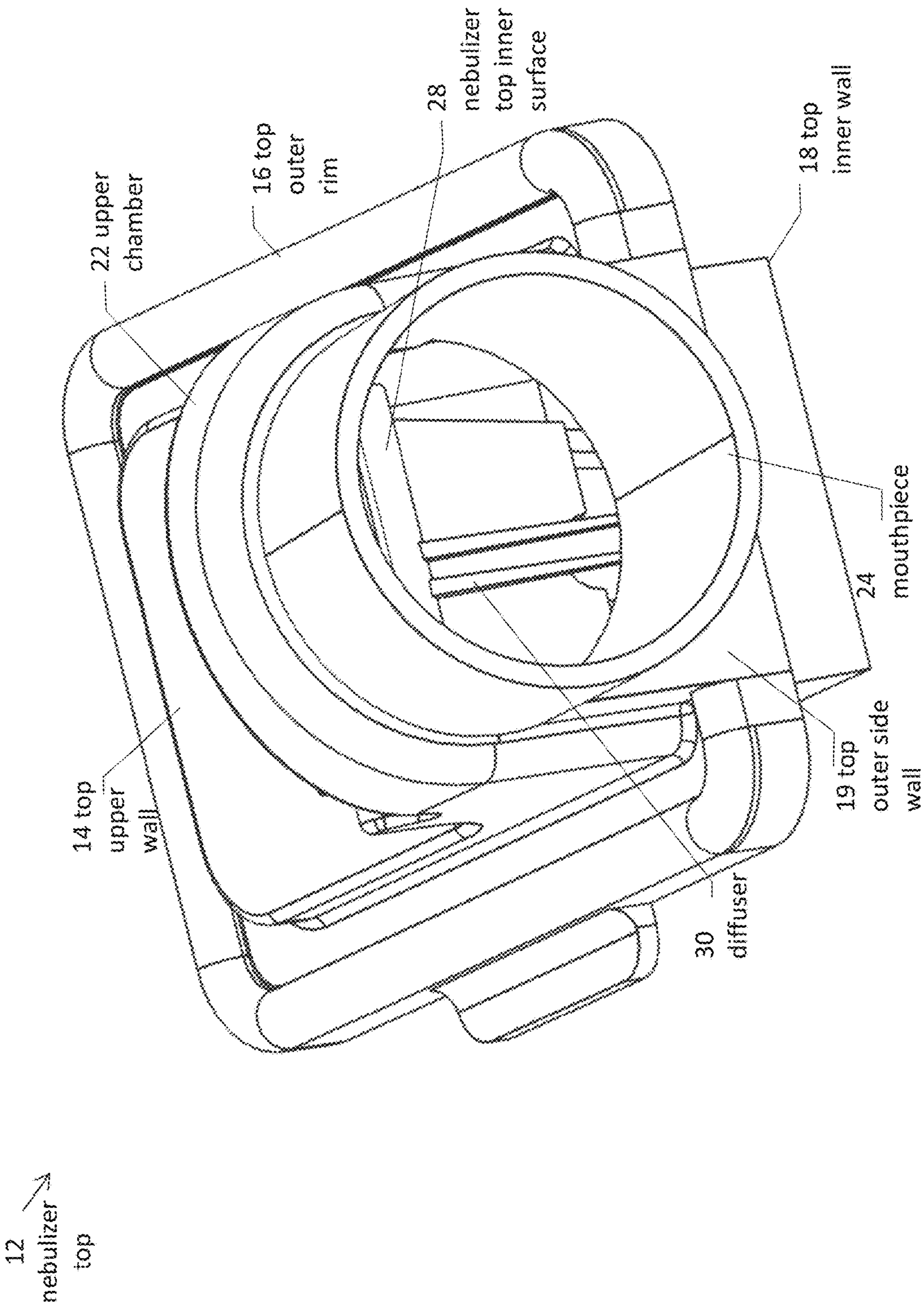
FIGS. 2 and 3 illustrate a nebulizer top in accordance with an example embodiment of the disclosure.
Figure 3:
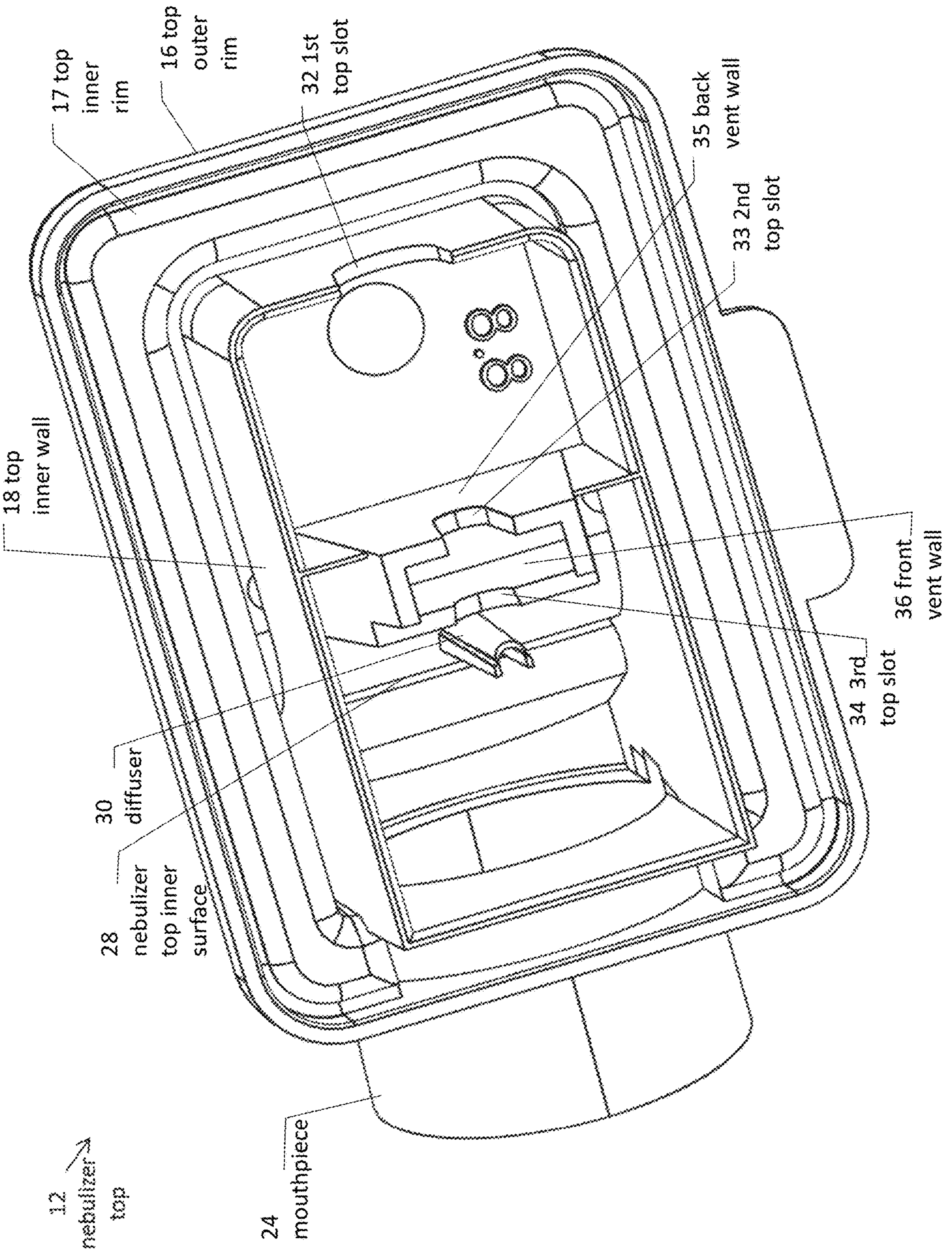
Figure 4:
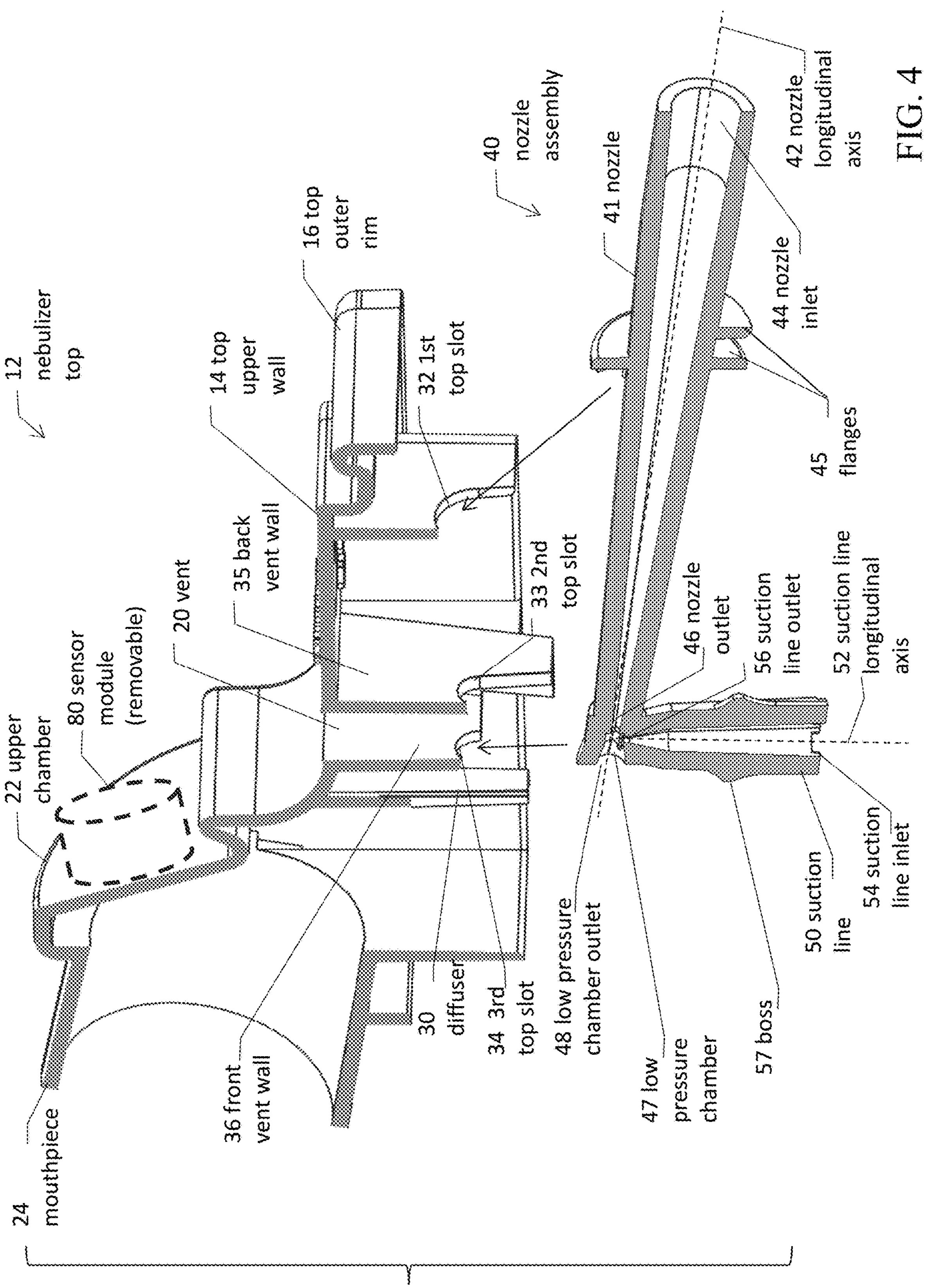
FIG. 4 illustrates a nebulizer top and a nozzle assembly in accordance with an example embodiment of the disclosure.
Figure 5:
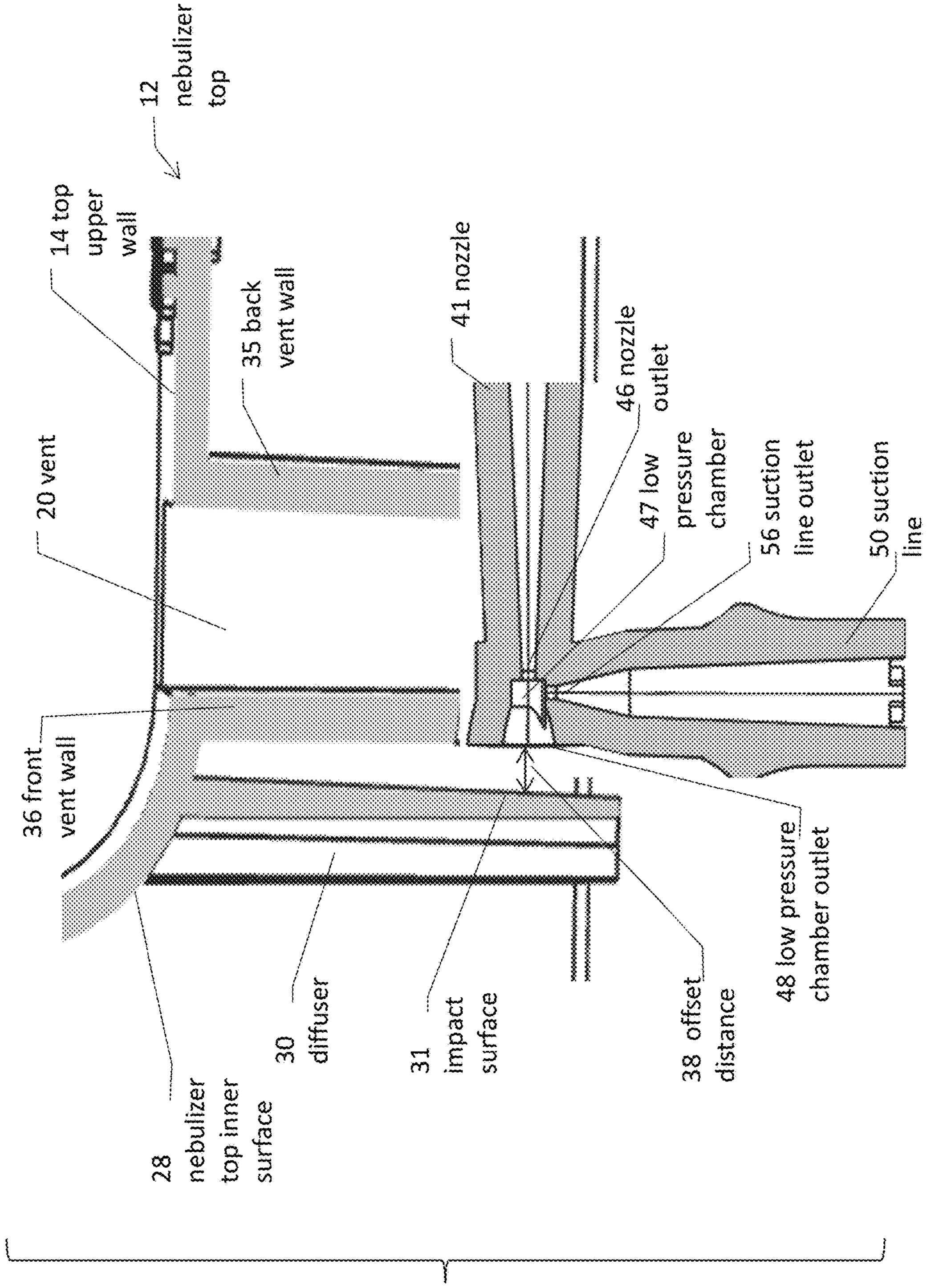
FIG. 5 illustrates an enlarged view of a portion of the nebulizer top and a portion of the nozzle assembly in accordance with an example embodiment of the disclosure.
Figure 6:
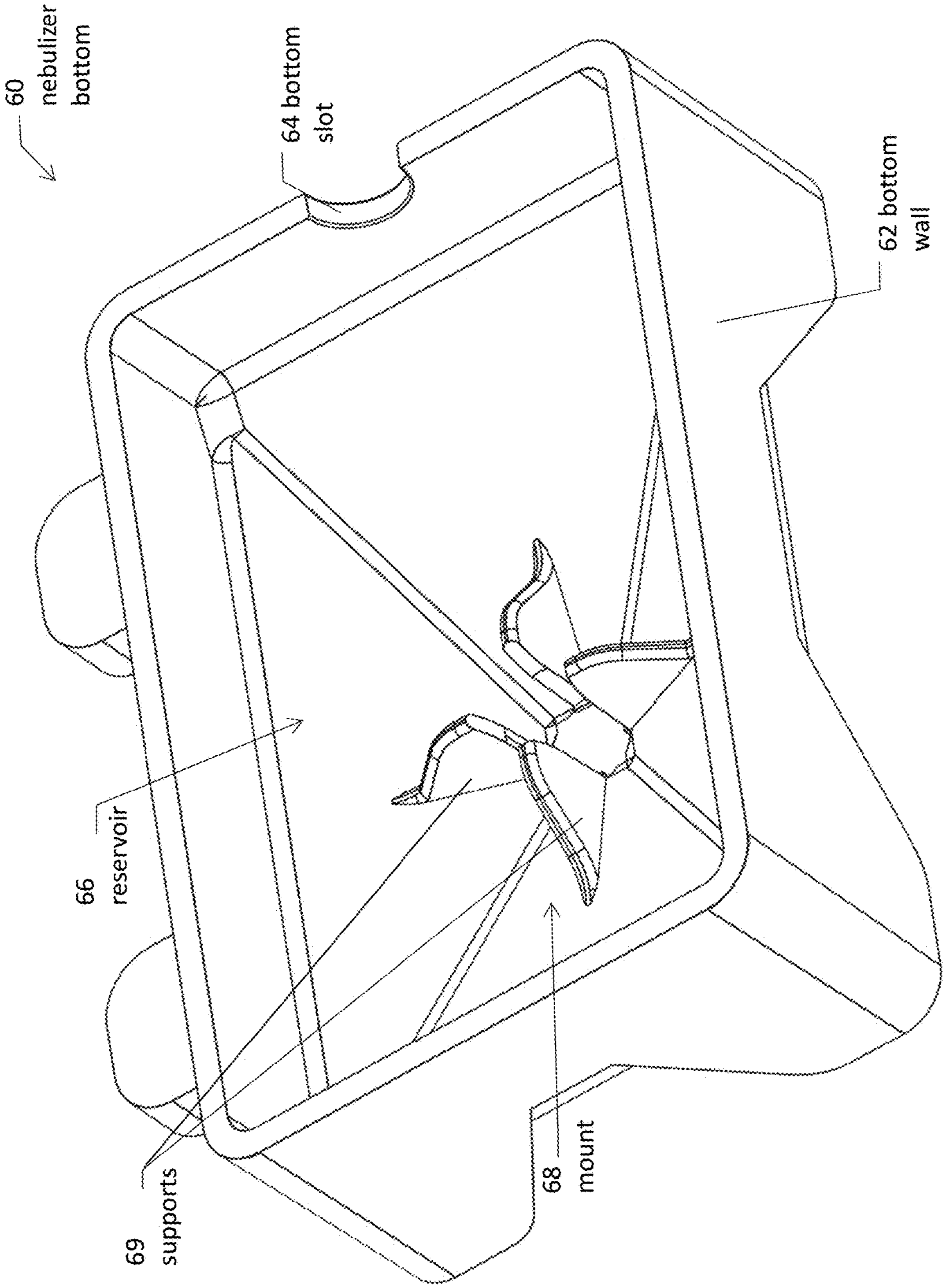
FIGS. 6 and 7 illustrate top and bottom views, respectively, of a nebulizer bottom in accordance with an example embodiment of the disclosure.
Figure 7:
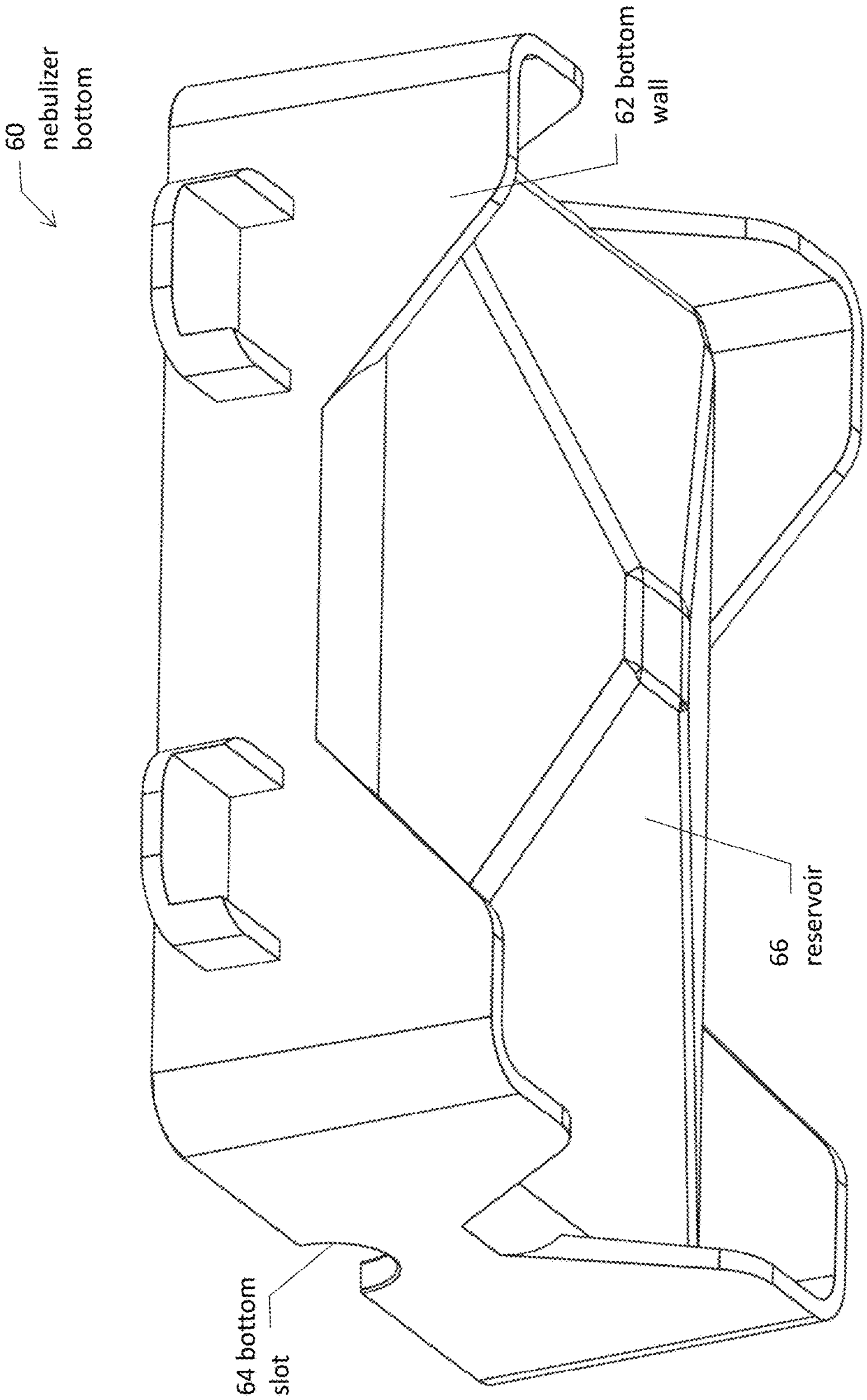

Referring now to FIG. 1, an exploded view of an example nebulizer 10 is illustrated. The nebulizer comprises a nebulizer top 12, a nebulizer bottom 60, and a nozzle assembly 40 that fits between the nebulizer top 12 and the nebulizer bottom 60. FIGS. 2-7 provide various views of components of the example nebulizer 10. Specifically, FIGS. 2 and 3 show top and bottom views, respectively, of the nebulizer top 12. FIGS. 4 and 5 illustrate the coupling of the nebulizer top 12 and the nozzle assembly 40. FIGS. 6 and 7 illustrate top and bottom views, respectively, of the nebulizer bottom 60. The features of the nebulizer 10 shown in FIGS. 1-7 and described further below are illustrative and in alternate embodiments certain features may be modified or omitted, while other features also may be added to the nebulizer.

Referring to FIGS. 1-7, the components of the nebulizer 10 are designed to facilitate interchangeability. That is, one or more of the nebulizer top 12, the nebulizer bottom 60, and the nozzle assembly 40 can be replaced with a counterpart nebulizer top, nebulizer bottom, or nozzle assembly that is similar in design, but that has one or more different properties. The one or more different properties can be selected to produce a target aerosol droplet size that is optimized for a particular application. The target aerosol droplet size can be a discrete size, such as 5 microns, or can be a size range, such as 0.5-5 microns. Medications administered to a patient using the nebulizer can have an optimal aerosol droplet size that improves the efficacy of the medication and/or minimizes waste of the medication. Properties of the medication, such as viscosity and density, can affect the aerosol droplet size. Accordingly, the nebulizer 10 allows for selection of components that will produce an aerosol droplet size that meets or approaches the target size for a particular medication.

FIGS. 1-5 illustrate features of the example nebulizer top 12. The nebulizer top 12 comprises a top upper wall 14 surrounded by a top outer rim 16. The top upper wall 14 has a generally horizontal planar portion and a curved portion that partially defines an upper chamber 22. The horizontal planar portion of the top upper wall 14 includes a vent 20 having an external aperture in the horizontal planar portion of the top upper wall 14 and having an internal aperture located proximate to a low pressure chamber outlet 48 of the nozzle assembly 40. The vent permits air to flow between an interior of the nebulizer 10 and the ambient environment surrounding the nebulizer 10. As will be described further below, the position of the vent 20 accelerates the flow of air through the nozzle assembly 40, thereby accelerating the aerosol droplets of medication toward the patient.

FIG. 4 illustrates a sensor module 80 attached to the exterior surface of the curved portion of the top upper wall 14. The sensor module 80 is shown in broken lines to indicate that it is an optional component which is not required in all embodiments of the nebulizer described herein. The sensor module 80 can be detachably coupled to the top upper wall 14 so that it can be replaced with other sensor modules or so that the nebulizer can be used without a sensor module in some instances. The sensor module 80 can include one or several sensors that detect signals corresponding to properties such as temperature, humidity, air pressure, air flow, a level of medication in the nebulizer bottom 60, biological characteristics of the patient, and characteristics of particles within the nebulizer 10. One or more apertures in the curved portion of the top upper wall 14 can allow sensors to collect data from the interior of the nebulizer 10 and, in some examples, allow one or more sensors to project through the top upper wall 14 and into the interior of the nebulizer 10 for the purpose of collecting data from the interior of the nebulizer. Additional aspects of the sensor module 80 will be described further in connection with subsequent figures.

The exterior of the nebulizer top 12 also includes a mouthpiece 24 at one end that is designed to fit within a patient's mouth. The mouthpiece 24 is mounted on a top outer side wall of the nebulizer top 12. The mouthpiece 24 has a generally cylindrical shape that is symmetrical about a mouthpiece axis 26. As shown in FIGS. 1, 2, and 4, the mouthpiece 24 can be oriented at an upward angle to facilitate use such that the mouthpiece axis 26 forms an obtuse angle with the horizontal planar portion of the top upper wall 14.

As illustrated in FIGS. 1 and 4, when the components of the nebulizer 10 are assembled, the nebulizer top 12 and the nebulizer bottom 60 are detachably coupled with the nozzle assembly 40 located therebetween. When the components of the nebulizer 10 are assembled, features on the interior of the nebulizer top 12 rest on a horizontal nozzle 41 of the nozzle assembly 40. Specifically, the nebulizer top 12 includes a top inner wall 18 that extends vertically downward from the inner surface of the top upper wall 14 and from the inner rim of the mouthpiece 24. The top inner wall 18 is encircled by the top outer rim 16 and by a top inner rim 17, the top inner rim 17 being disposed within the top outer rim 16 and generally mirroring the shape of the top outer rim 16. The top inner wall 18 includes a first top slot 32 located adjacent the end of the nebulizer top 12 that is opposite the mouthpiece 24. The first top slot 32 rests on top of the nozzle 41 when the two components are coupled together. Similarly, a front vent wall 36 and back vent wall 35 define the vent 20 and extend vertically downward from the inner surface of the top upper wall 14. The back vent wall 35 has a second top slot 33 and the front vent wall 36 has a third top slot 34 that rest on top of the nozzle 41 when the two components are coupled together. The configuration of the first top slot 32, second top slot 33, and third top slot 34 allows the nebulizer top 12 and the nozzle assembly 40 to be easily coupled and decoupled so that the nozzle assembly 40 can be replaced with another nozzle assembly having different dimensions that provides a different aerosol droplet size. The upwardly pointing arrows in FIG. 4 illustrate the placement of the nozzle assembly 40 into the first top slot 32, the second top slot 33, and the third top slot 34. While the example nebulizer 10 of FIG. 4 illustrates three top slots into which the nozzle assembly 40 fits, it should be understood that other arrangements of slots and a greater or fewer number of top slots can be implemented in other embodiments for securing the nozzle assembly to the nebulizer top.

Also illustrated in FIGS. 2, 3, 4, and 5 is a diffuser 30 suspended from the nebulizer top inner surface 28. The diffuser projects generally in a downward vertical direction so that it is disposed adjacent to a low pressure chamber outlet 48 of the nozzle assembly 40 when the nozzle assembly and the nebulizer top 12 are coupled together. The diffuser 30 has an impact surface 31, which is the surface facing towards and closest to the low pressure chamber outlet 48. As illustrated in the enlarged view provided in FIG. 5, the shortest distance between the impact surface 31 of the diffuser 30 and the low pressure chamber outlet 48 is called the offset distance 38. Aerosol droplets of medication that exit the low pressure chamber outlet 48 and strike the impact surface 31 generally break up into smaller sized aerosol droplets. Generally, a shorter offset distance 38 increases the likelihood that aerosol droplets will strike the impact surface 31 of the diffuser and break up into smaller sized aerosol droplets. The nebulizer 10 facilitates control of the aerosol droplet size in that the nebulizer top 12 can be replaced by a second nebulizer top, such as the nebulizer top 112 of FIG. 8, with a second diffuser having a second offset distance that is different than the offset distance 38 of diffuser 30. Accordingly, the aerosol droplet size can be controlled by selecting a nebulizer top having a diffuser with a desired offset distance from the low pressure chamber outlet 48. While the diffuser 30 is shown suspended from the nebulizer top inner surface 28 in the example of FIGS. 2, 3, 4, and 5, in alternate embodiments the diffuser can be mounted on the nebulizer bottom 60 so that it projects vertically upward from the nebulizer bottom 60 to the low pressure chamber outlet 48.

Turning to the nozzle assembly 40, as illustrated in FIGS. 1 and 4, the nozzle assembly comprises the nozzle 41 and a suction line 50 that are oriented generally perpendicular to each other. When the nebulizer is in use delivering nebulized medication to a patient, the nozzle 41 is in a generally horizontal position and the suction line 50 is in a generally vertical position. The nozzle 41 is an elongate tube with an interior channel having a nozzle inlet 44 at one end of the interior channel and a nozzle outlet 46 at the opposite end of the interior channel. A nozzle longitudinal axis 42 passes through the center of the nozzle inlet 44 and the center of the nozzle outlet 46. The exterior surface of the nozzle 41 includes a pair of flanges 45 that secure the nozzle assembly 40 in the proper position when the nebulizer 10 is assembled. Specifically, on the bottom side of the nozzle 41, the pair of flanges 45 rest on either side of a bottom slot 64 of the nebulizer bottom 60 thereby holding the nozzle assembly 40 in the proper position when it is placed between the nebulizer top 12 and the nebulizer bottom 60. As illustrated in FIGS. 1 and 4, at least one of the flanges also can extend around the outer circumference of the nozzle 41 to the top side of the nozzle 41 so that the flange will rest against the top inner wall 18 when the nozzle 41 is positioned in the first top slot 32.

When the nebulizer 10 is in use, a supply of gas, such as air, is coupled to the nozzle inlet 44 to force gas through the nozzle 41 towards the nozzle outlet 46. For example, the gas supply can be a pump or a canister of pressurized gas. The interior channel of the nozzle 41 is shaped such that the nozzle outlet 46 is narrower than the nozzle inlet 44. This narrowing shape of the interior channel causes a phenomenon known as the Venturi effect whereby the air flowing from the gas supply through the interior channel accelerates and causes a zone of low pressure at the nozzle outlet 46.

The nozzle assembly also comprises a low pressure chamber 47 where the nozzle outlet 46 and the suction line outlet 56 intersect. The low pressure chamber 47 is a zone of low pressure resulting from the air passing through the aperture at the nozzle outlet 46, which is narrower than the aperture at the nozzle inlet 44. The zone of low pressure draws medication up the suction line 50 and into the low pressure chamber 47 wherein the low pressure condition causes the medication to nebulize into an aerosol of small droplets. The low pressure chamber 47 also has a low pressure chamber outlet 48 through which the aerosol droplets exit the nozzle assembly 40 and travel towards the mouthpiece 24. The low pressure chamber 47 and low pressure chamber outlet 48 are proximate to the interior aperture of the vent 20 when the nozzle assembly 40 is positioned in the first top slot 32, the second top slot 33, and the third top slot 34 as illustrated by the upward arrows in FIG. 4. As explained previously, the position of the vent 20 further increases the drop in pressure at the low pressure chamber 47 and further accelerates the aerosol droplets of medicine exiting the low pressure chamber outlet 48.

Somewhat similar in shape to the nozzle 41, the suction line 50 is an elongate tube with an interior channel having a suction line inlet 54 at one end of the interior channel and a suction line outlet 56 at the opposite end of the interior channel. A suction line longitudinal axis 52 passes through the center of the suction line inlet 54 and the center of the suction line outlet 56. When the three components of the nebulizer 12 are assembled, the suction line 50 will sit in a reservoir 66 of the nebulizer bottom 60 with the suction line inlet 54 submerged in the medicine within the reservoir 66. The zone of low pressure at the low pressure chamber 47 will draw medicine from the reservoir 66, up through the interior channel of the suction line 50, through the suction line outlet 56, and into the low pressure chamber 47 where the medicine is mixed with the flow of gas from the nozzle 41 and the low pressure condition nebulizes the medicine into an aerosol of droplets. Similar to the nozzle 41, the interior channel of the suction line 50 can be narrower near the suction line outlet 56 than at the suction line inlet 54 to take advantage of the Venturi effect which accelerates the medicine as it is drawn up through the suction line 50. As will be described further in connection with FIGS. 6 and 7, the exterior surface of the suction line 50 includes multiple bosses 57 that assist in mounting the suction line 50 in the proper position in the nebulizer bottom 60.

Referring again to FIGS. 1-4, when the nebulizer 10 is assembled and used to deliver a medication to a patient, a gas such as air is provided by a gas supply to the nozzle inlet 44. The rate of gas flow into the nozzle inlet 44 can be selected based upon the dimensions of the nebulizer and the properties of the medication that is to be nebulized. Example rates for the gas flow from the gas supply into the nozzle inlet 44 can range from less than 1 liter per minute up to 15 liters per minute. The narrowing of the interior channel of the nozzle 41 as the gas travels from the nozzle inlet 44 to the nozzle outlet 46 causes the gas to accelerate and produces a low pressure condition at the low pressure chamber 47. In other words, the low pressure condition is a differential in the pressure at the low pressure chamber 47 relative to the pressure in the reservoir 66 where the medication is located. The low pressure condition created when the gas flows from the gas supply through the nozzle 41 can be referred to as the initial pressure. A typical range for the initial pressure can be −1 to −3 cmH2O. However, the nebulizer can be configured so that medicine is drawn up through the suction line 50 and nebulized only upon the pressure in the low pressure chamber 47 dropping below an activation pressure. In other words, the nebulizer is configured so that the initial pressure is insufficient to draw the medicine up through the suction line 50. The activation pressure, which can be in the range from −3 to −52 cmH2O, can be achieved when the patient inhales with the nebulizer positioned in the patient's mouth. The activation pressure in the low pressure chamber 47 is achieved by the gas flow from the gas supply through the nozzle 41 in combination with patient's inhalation. Configuring the nebulizer so that the activation pressure is achieved only when the patient inhales in combination with the gas flow reduces the nebulization of medicine when the patient is not inhaling and, therefore, reduces wasting of the medicine.

Once the activation pressure is achieved, the pressure differential between the low pressure chamber 47 and the reservoir 66 causes the medicine to be drawn up through the suction line 50 where it mixes with the gas flowing through the nozzle 41 and where it is nebulized into an aerosol of droplets. As illustrated in FIG. 5, the gas flowing through the nozzle 41 pushes the aerosol of medicine droplets out the low pressure chamber outlet 48 where they collide with the impact surface 31 of the diffuser 30. The collision with the impact surface 31 causes the medicine droplets to break up into smaller droplets thereby promoting inhalation into the lungs. After encountering the diffuser 30, the aerosol of droplets flow through the upper chamber 22 toward the mouthpiece 24. The upper chamber 22 is located between the interior aperture of the mouthpiece 24 and the curved portion of the top upper wall 14. When the nebulizer is being used with the patient, the upper chamber 22 is located in an elevated position that is above the low pressure chamber outlet 48 and the impact surface 31 of the diffuser. The elevated position of the upper chamber 22 causes larger droplets of medicine to fall back down into the reservoir 66 due to the force of gravity, while smaller droplets of medicine will continue to flow to the mouthpiece 24. Thus, the design of the upper chamber 22 is advantageous because generally it is preferable to have the patient inhale relatively smaller droplets of medicine that are more likely to be inhaled into the lungs, whereas larger droplets are more likely to be lodged in the patient's mouth and throat.

The mouthpiece 24 has a generally cylindrical shape and is sized to fit into the patient's mouth. The mouthpiece 24 rests on the top outer side wall 19 and has an inner aperture adjacent to the upper chamber 22 and an outer aperture that fits into the patient's mouth. The mouthpiece 24 is positioned in proximity to the low pressure chamber outlet 48 and the diffuser 30 to minimize the distance that the medicine droplets must travel to reach the patient's mouth and lungs. When the medicine droplets have a greater distance to travel, it increases the likelihood that the droplets will collide with each other and combine into larger droplets which are less desirable. Accordingly, to promote smaller droplet sizes and the uptake of the medicine, the mouthpiece 24 is in close proximity to the low pressure chamber outlet 48 and the diffuser 30.

Referring now to FIGS. 6 and 7, the nebulizer bottom 60 is illustrated in greater detail. The nebulizer bottom 60 comprises a bottom wall 62 around the perimeter of the nebulizer bottom 60 that surrounds a reservoir 66. Although not shown in FIGS. 6 and 7, the reservoir 66 will be filled with the liquid medicine that will be nebulized and administered to the patient. The bottom wall comprises a bottom slot 64 that receives the bottom side of the nozzle 41 when the nebulizer bottom 60, the nozzle assembly 40, and the nebulizer top 12 are coupled together in accordance with the arrangement illustrated in FIG. 1. In the bottom of the reservoir 66 is a mount 68 that comprises a plurality of projecting supports 69. The supports 69 are configured to receive the suction line 50 when the nebulizer bottom 60, the nozzle assembly 40, and the nebulizer top 12 are coupled together in accordance with the arrangement illustrated in FIG. 1. The supports 69 are shaped so that they engage the bosses 57 located on the exterior of the suction line 50. In alternate embodiments of the nebulizer, the configuration of the bottom slot 64 and the mount 68 can be modified to receive nozzle assemblies having other shapes and sizes.

The example nebulizer bottom illustrated in FIGS. 6 and 7 can be replaced with other types of nebulizer components that supply medication to the nebulizer. As one example, the nebulizer bottom can comprise a piercing mechanism to which a medicine ampule is attached. The medicine ampule can be a sealed container containing one or more doses of a medicine and when the medicine is exhausted, the medicine ampule can be removed and replaced with a new medicine ampule.

The nebulizer illustrated in FIGS. 1-7 is an example of an intra-oral nebulizer in that the medication is nebulized proximate to the opening of the patient's mouth. However, it should be understood that the components of the example nebulizer can be modified so that the nebulizer can be used as a ventilator nebulizer or a metered dose nebulizer.

Referring now to FIGS. 8, 9A, 9B, and 9C, the interchangeability of the components of the nebulizer will be described in further detail. As referenced previously, an advantage of the design of the nebulizer embodiments described herein is that one or more of the components of the nebulizer can be interchanged with a similar counterpart component. The similar counterpart component can have one or more different properties, such as different dimensions, different configurations, or different textures that result in a change in the performance of the nebulizer. Because the droplet size of the nebulized medicine is critical to effective delivery of the medicine into the patient's lungs, the ability to control the droplet size by customizing the configuration of the nebulizer provides a significant advantage.

Figure 8:
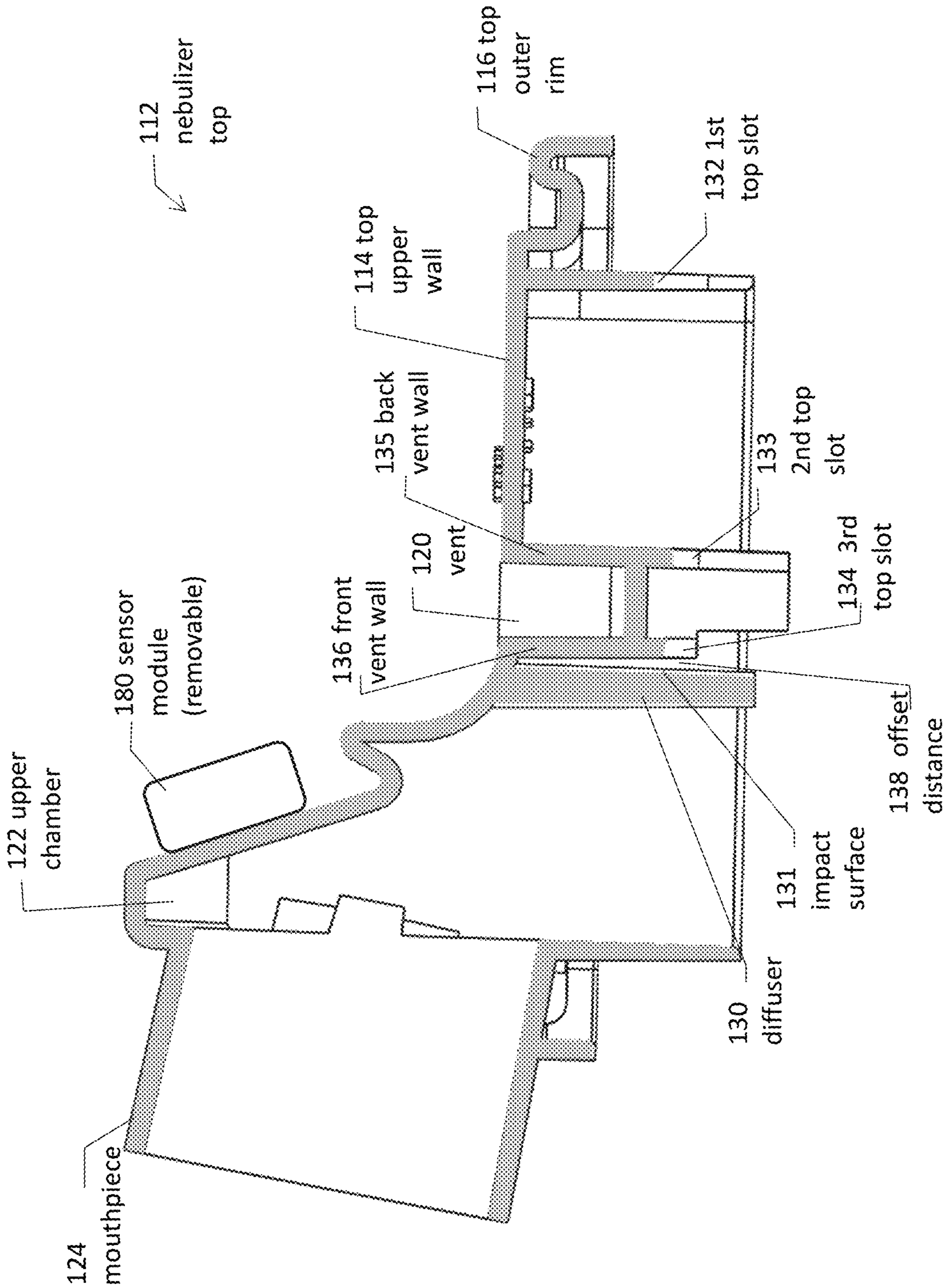
FIG. 8 illustrates a cross-sectional view of another nebulizer top in accordance with an example embodiment of the disclosure.

As one example, a user, such as a medicine provider, a health care provider, or a patient, can replace the nebulizer top 12 of the embodiment illustrated in FIGS. 1-5 with counterpart nebulizer top 112 illustrated in FIG. 8. Counterpart nebulizer top 112 has features similar to those of nebulizer 12 so that it can couple to the nozzle assembly 40 and the nebulizer bottom 60. Nebulizer top 112 comprises a top outer rim 116 surrounding a top upper wall 114. The top upper wall 114 comprises a horizontal planar portion and a curved portion that partially defines an upper chamber 122 and that supports a removable sensor module 180. The top upper wall 114 has an exterior opening of a vent 120, the vent 120 partially defined by a front vent wall 136 and a back vent wall 135. Similar to the nebulizer top 12, the nebulizer top 112 comprises a first top slot 132, a second top slot 133, and a third top slot 134 that receive a nozzle assembly. A diffuser 130 extends downward from a top inner surface of the nebulizer top 112 and has an impact surface 131. The position of the impact surface 131 of the diffuser 130 defines an offset distance 138 from a low pressure chamber outlet of a nozzle assembly that can be coupled to the nebulizer top 112. Lastly, a mouthpiece 124 is shaped to fit within a patient's mouth and deliver nebulized medication. The descriptions provided above of the components of nebulizer top 12 in connection with FIGS. 1-5 generally apply to the counterpart components of nebulizer top 112 that have the same last two digits in their reference numbers. Accordingly, those further descriptions will not be repeated for nebulizer top 112.

However, nebulizer top 112 can have one or more properties that are different from the properties of nebulizer top 12 thereby producing a different result when the nebulizer is operated. Examples of properties that can be different in nebulizer top 112 relative to nebulizer top 12 include the shape of the vent 120, the size and shape of the mouthpiece 124, and the shape, texture, or position of the diffuser 130. Taking the example of the position of the diffuser 130, replacing nebulizer top 12 with nebulizer top 112 wherein the diffuser 130 is positioned closer to the nozzle assembly reduces the offset distance and generally has an effect of producing smaller sizes of the nebulized medicine droplets. As another example, the density or viscosity of a particular medicine may call for a diffuser having a different shape or texture to optimize delivery of the medication to the patient.

Figure 9A:
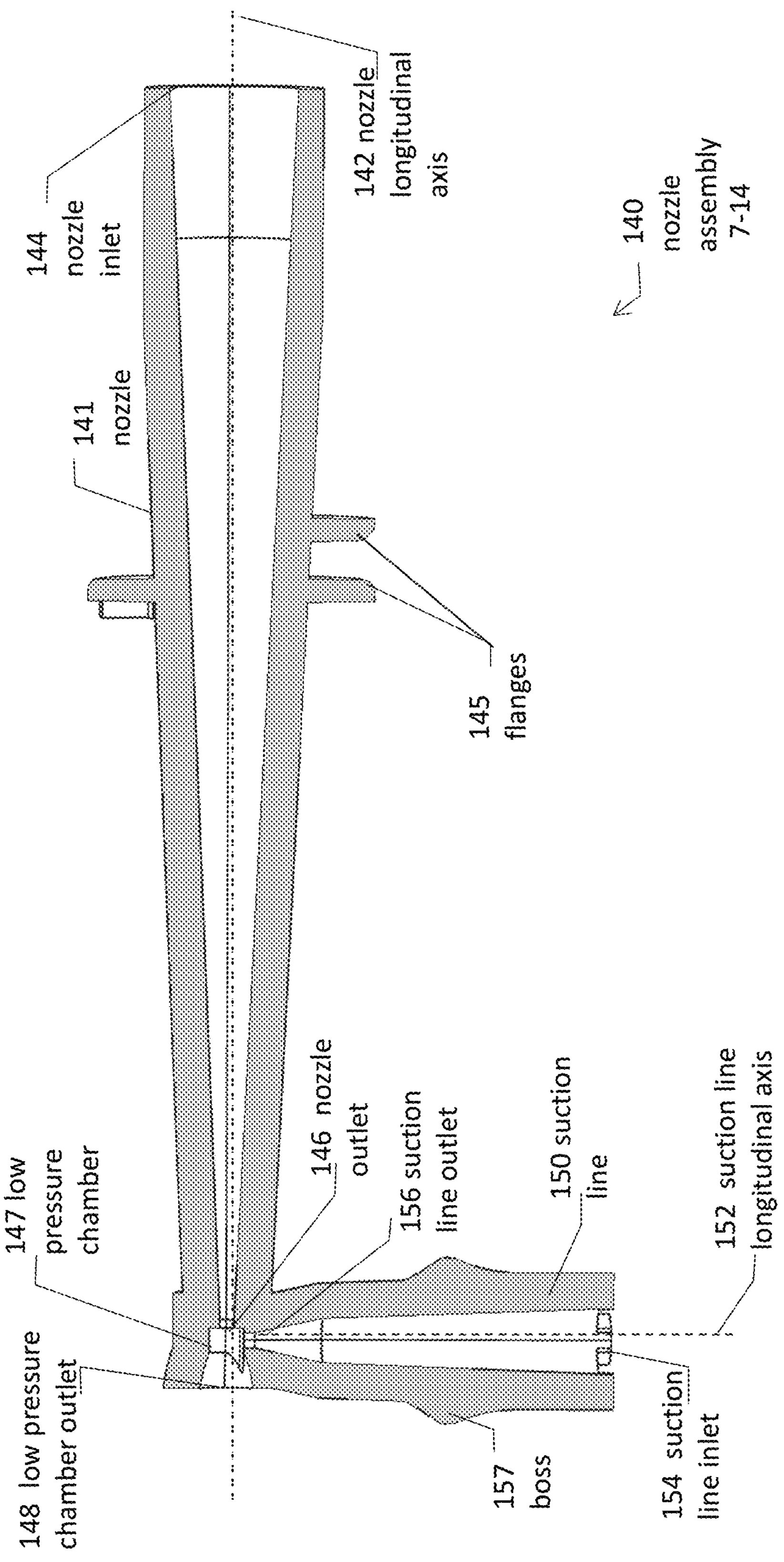
FIGS. 9A, 9B, and 9C illustrate nozzle assemblies having differing properties in accordance with an example embodiment of the disclosure.
Figure 9B:
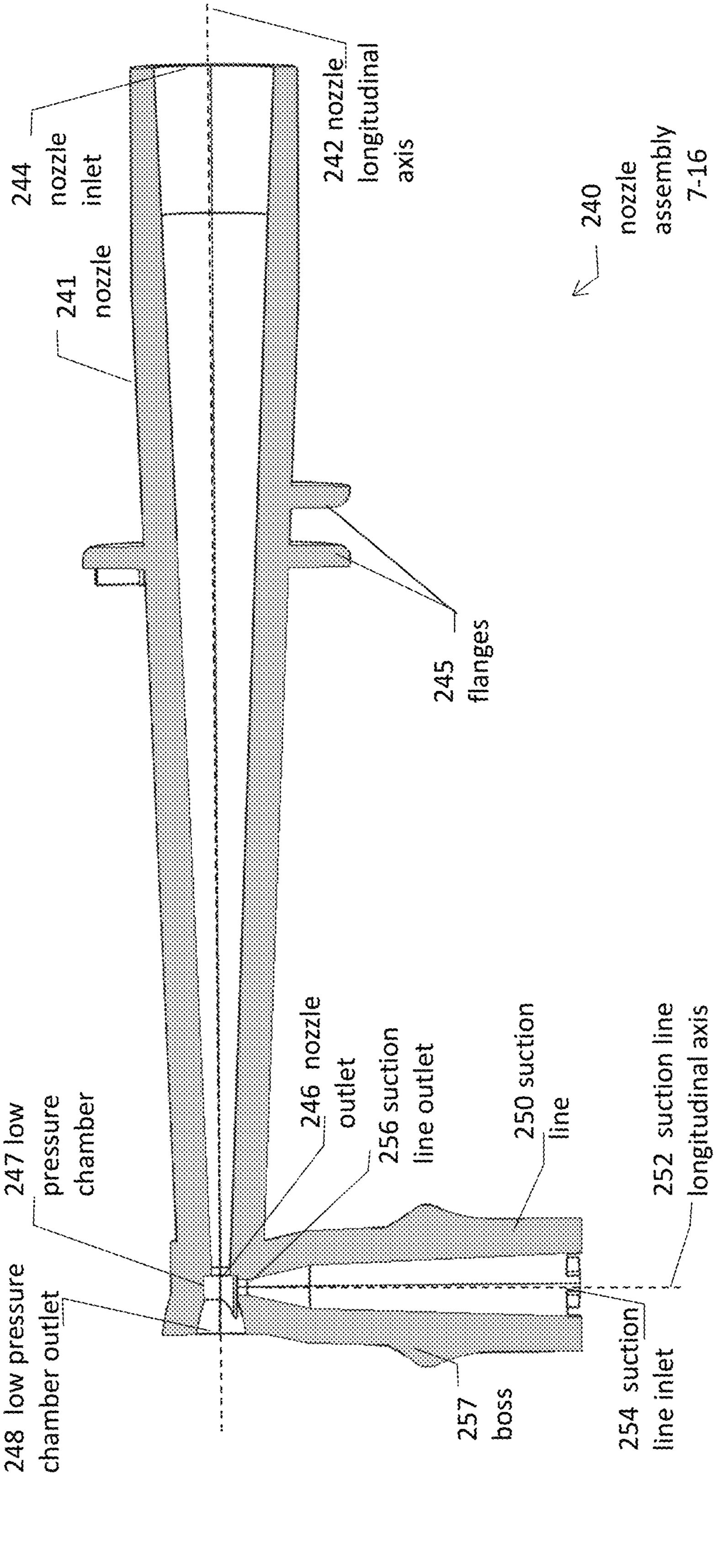
Figure 9C:
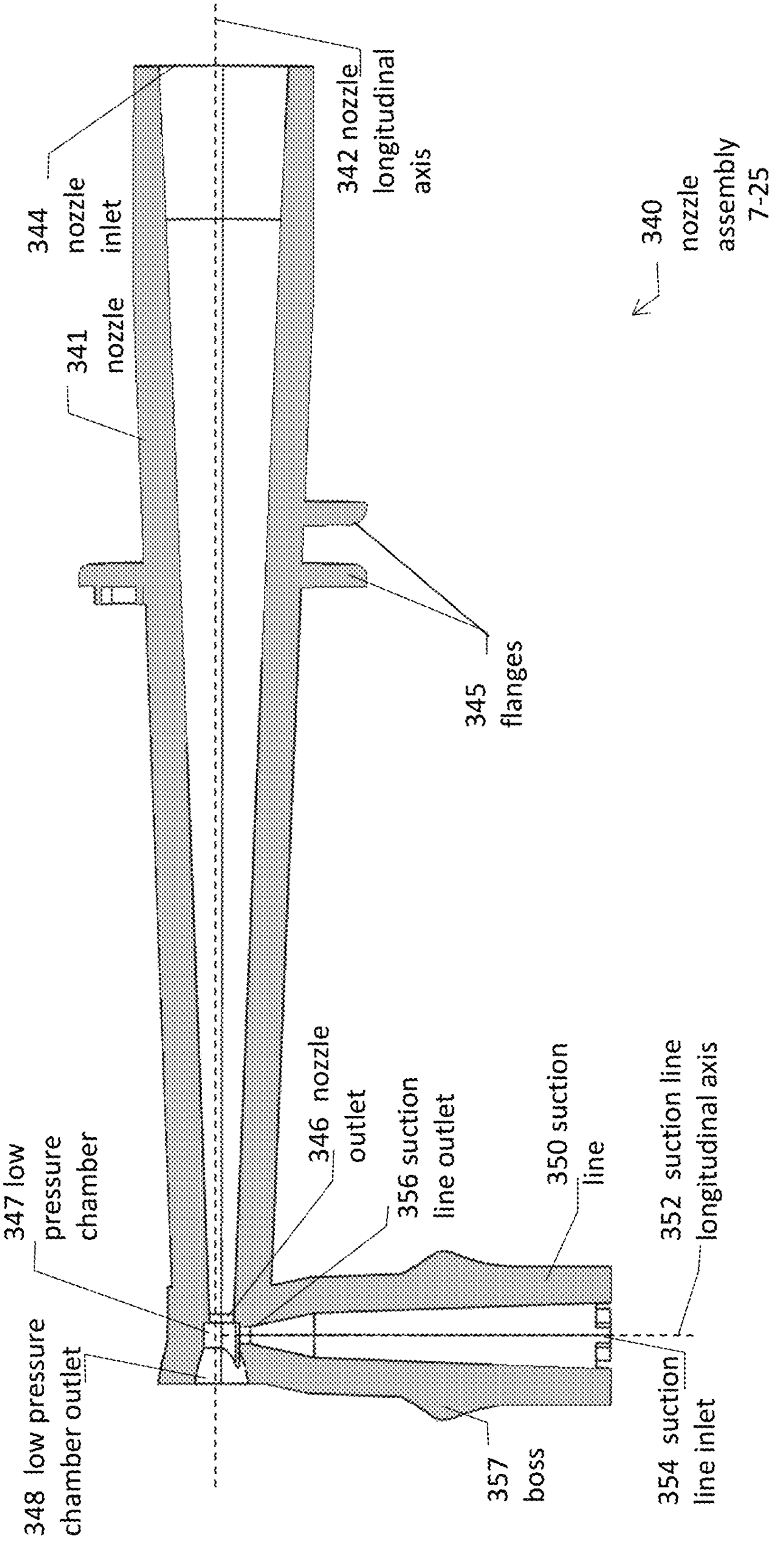

In another example of the interchangeability of the components of the nebulizer, as an alternative to replacing the nebulizer top, the user may replace the nozzle assembly 40 with a counterpart nozzle assembly, such as one of the nozzle assemblies illustrated in FIGS. 9A, 9B, and 9C. Counterpart nozzle assemblies 140, 240, and 340 of FIGS. 9A, 9B, and 9C, respectively, have features similar to nozzle assembly 40 so that they can easily couple to a nebulizer top and a nebulizer bottom in a manner similar to that described in connection with FIGS. 1-7. Nozzle assembly 140 comprises a nozzle 141 oriented generally perpendicularly to a suction line 150. Nozzle 141 comprises an interior channel having a nozzle inlet 144 at one end and a narrower nozzle outlet 146 at the opposite end. A nozzle longitudinal axis 142 passes through the center of the nozzle inlet 144 and the nozzle outlet 146. Similarly, the suction line 150 comprises an interior channel having a suction line inlet 154 at one end and a narrower suction line outlet 156 at the opposite end. A suction line longitudinal axis 152 passes through the center of the suction line inlet 154 and the suction line outlet 156. The nozzle assembly 140 further comprises a low pressure chamber 147 where the nozzle outlet 146 and the suction line outlet 156 intersect. When a nebulizer is operating, a pressure differential referred to as an activation pressure in the low pressure chamber 147 causes medication to be drawn up through the suction line 150 from a reservoir wherein the medication mixes with a gas flowing through the nozzle 141 and nebulizes to form an aerosol of medication droplets that exit through a low pressure chamber outlet 148. Lastly, the suction line includes bosses 157 that assist in mounting the nozzle assembly 140 in the reservoir and the bottom surface of the nozzle 141 includes flanges 145 that assist in mounting the nozzle assembly to a nebulizer bottom. The descriptions provided above of the components of nozzle assembly 40 in connection with FIGS. 1, 4, and 5 generally apply to the counterpart components of nozzle assembly 140 that have the same last two digits in their reference numbers. Accordingly, those further descriptions will not be repeated for nozzle assembly 112.

FIG. 9B illustrates nozzle assembly 240 and FIG. 9C illustrates nozzle assembly 340. The components of nozzle assembly 240 and nozzle assembly 340 are generally similar to the components of nozzle assembly 40 and nozzle assembly 140 that have the same last two digits in their reference numbers. Accordingly, further descriptions of the components of nozzle assembly 240 and nozzle assembly 340 will not be repeated.

However, although the components of the foregoing nozzle assemblies are generally similar, each can have a unique property which produces a different result when the nebulizer is operated. Examples of properties that can be different among the example nozzle assemblies include the size of the nozzle outlet, the size of the suction line outlet, and the size of the low pressure chamber. As such, a nozzle assembly can be selected having properties optimized for the density or viscosity of the medicine, thereby producing medicine droplet sizes that improve the delivery of the nebulized medication to the patient.

Figure 10:
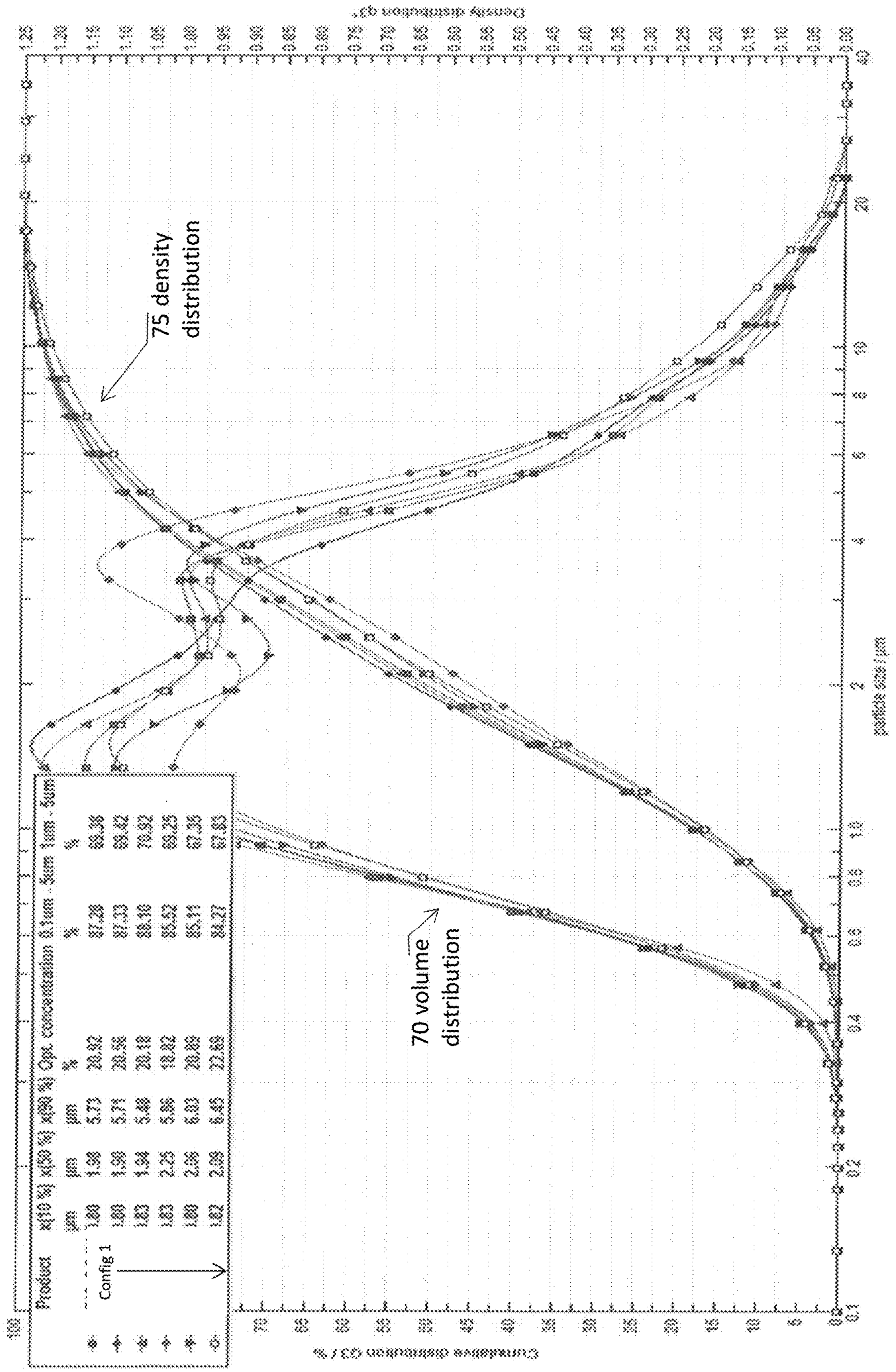
FIGS. 10 and 11 illustrate data showing the effect of nebulizer properties on aerosol droplet size in accordance with an example embodiment of the disclosure
Figure 11:
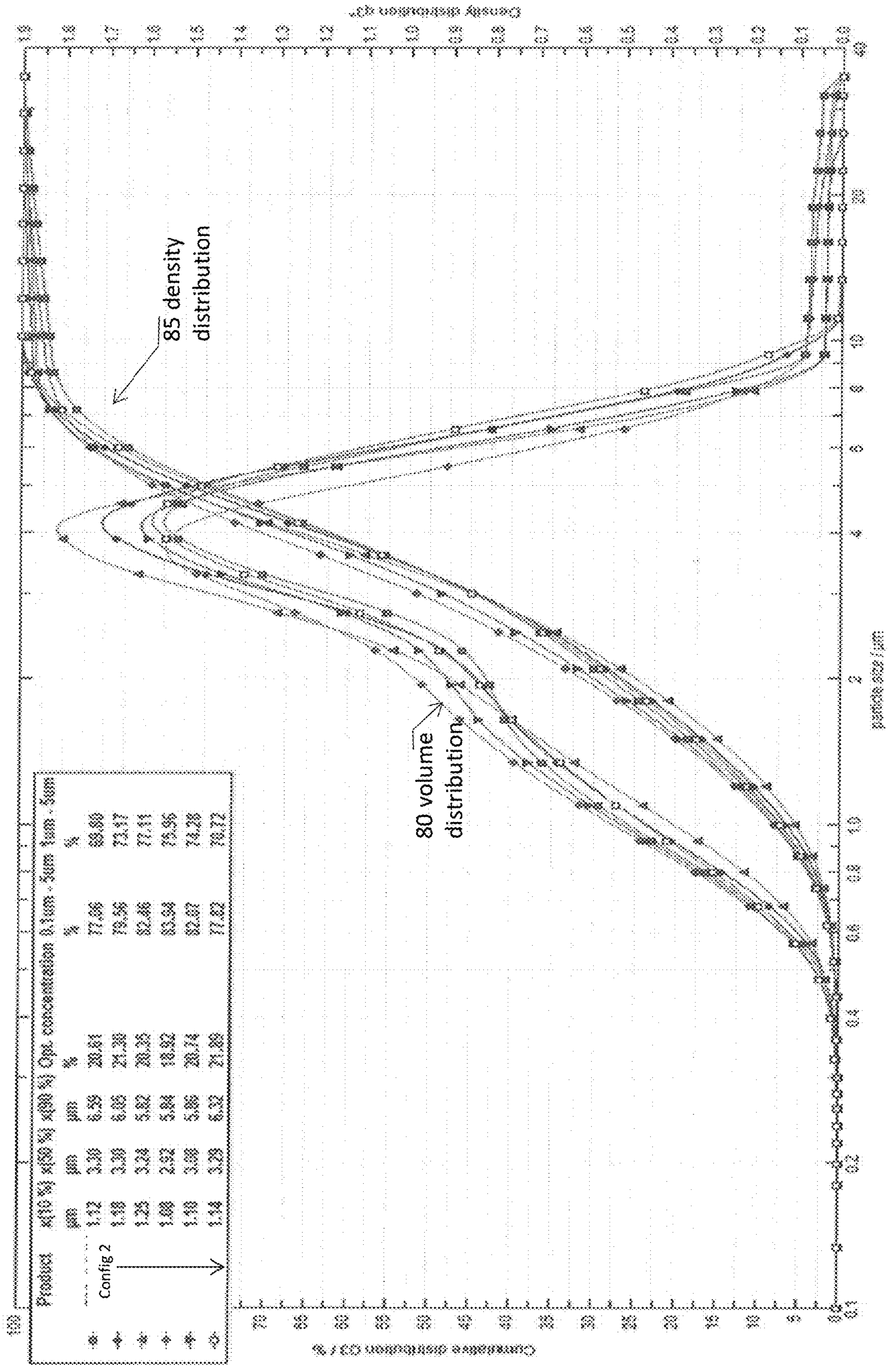

FIGS. 10 and 11 provide examples of test data collected from two different configurations of the components of a nebulizer for a medicine having a particular density and viscosity. The test data illustrate that modifying a property of the components of the nebulizer, such as the offset distance, the nozzle outlet size, the suction line outlet size, or the size of the diffuser, effects the size of the droplets in the nebulized medication. Referring to FIG. 10, the test data for a first configuration of a nebulizer shows a median droplet size ranging from 1.90 microns to 2.25 microns and the data further shows the percentage of particles in the test sample falling in the range from 0.1 microns to 5 microns ranges from 84.27% to 88.10%. In comparison, referring to FIG. 11, the test data for a second configuration of a nebulizer shows a median droplet size ranging from 2.92 microns to 3.30 microns and the data further shows the percentage of particles in the test sample falling in the range from 0.1 microns to 5 microns ranges from 77.06% to 83.94%. Accordingly, if the goal for the tested medication is a smaller droplet size, the test data indicates the first nebulizer configuration provides better results that the second nebulizer configuration. Given that a variety of variables involving the medicine and the properties of the nebulizer can affect the performance of the nebulizer, similar additional testing can be used to generate look-up tables showing the performance of different nebulizer configurations. Such look-up tables can be used by a medication provider, a health care provider, or the patient to select the optimal nebulizer configuration.

Referring now to FIGS. 12-17, the functionality of the nebulizer's sensor module will be described in greater detail. As referenced previously, the sensor module can be attached to the nebulizer and can include one or more sensors for collecting data associated with the nebulizer. Previously described FIGS. 4 and 8 include examples of a sensor module 80 and a sensor module 180, respectively. In certain example embodiments, the sensor module can be detachably coupled to the nebulizer so that it can be easily replaced, adjusted, or maintained. Alternatively, in certain embodiments the sensor module can be permanently attached to the nebulizer. As illustrated in FIGS. 4 and 8, it is preferred that the sensor module attaches to the component of the nebulizer that also comprises the mouthpiece. Taking the examples illustrated in FIGS. 4 and 8, the nebulizer top, which includes the mouthpiece and the sensor module, can be kept by the user for repeated uses, whereas other components of the nebulizer such as the nozzle assembly and/or the nebulizer bottom can be replaced after use or from time to time. For example, the nebulizer bottom can be a disposable component containing a single dose of medicine wherein the nebulizer bottom is disposed of after the single dose of medicine is administered to the patient and the next dose of medicine for the patient would be provided with a new replacement nebulizer bottom.

As illustrated in the example of FIG. 4, it is preferred that the sensor module 80 is located proximate to the mouthpiece 24 as that is the optimal location for collecting data relevant to the nebulizer. Positioning the sensor module 80 on the curved portion of the top upper wall 14 adjacent to the upper chamber 22 is advantageous because the one or more sensors of the sensor module can collect data relating to the nebulized aerosol of medication as it is inhaled by the patient and exits the nebulizer 10 through the mouthpiece 24 and can collect data relating to the patient's exhalation back into the nebulizer 10. The position of the sensor module 80 is also advantageous because there is a line of sight to the reservoir 66 in the nebulizer bottom 60 that allows for monitoring the medication in the reservoir. In some examples, one or more sensors of the sensor module can extend into the upper chamber 22 towards the mouthpiece 24 or towards the nebulizer bottom 60. While a single sensor module is illustrated in the examples of FIGS. 4 and 8, in other embodiments there can be multiple sensor modules at various locations on the nebulizer. Moreover, the functionality associated with the sensor module can be distributed among separate components such that, as one example, a sensor is located in the sensor module 80, but a processor and/or transmitter that receives the data collected by the sensor is located at a different position on the nebulizer.

Figure 12:
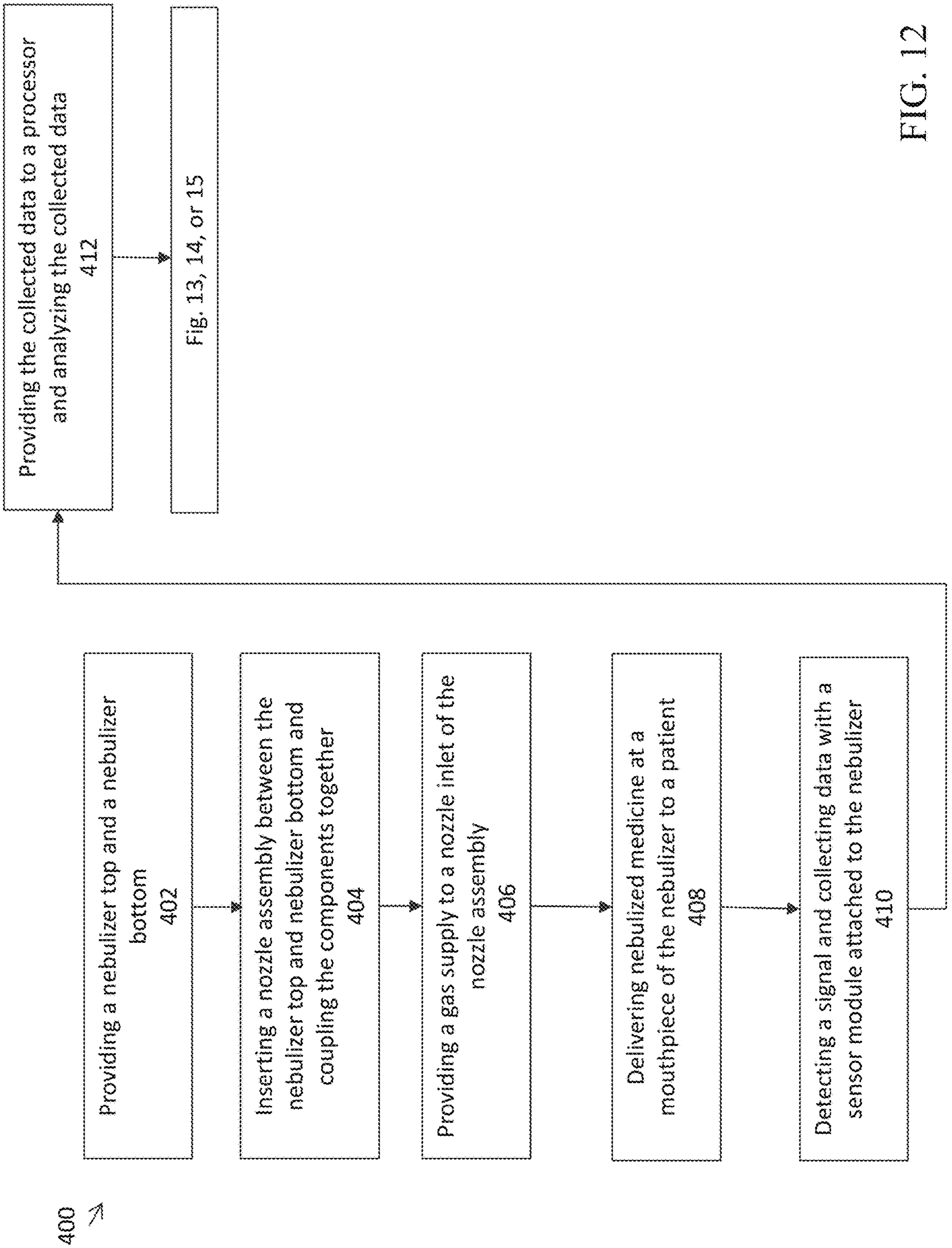
FIG. 12 illustrates a method of using a nebulizer in accordance with an example embodiment of the disclosure.

Referring now to FIG. 12, an example method 400 of using the nebulizer's sensing capabilities is illustrated. Beginning with operation 402, consistent with the configurable nebulizers described herein, a user can provide a nebulizer top and a nebulizer bottom. As explained previously, the user can be a medication supplier, a healthcare provider, or a patient. In operation 404, a user inserts a nozzle assembly between the nebulizer top and the nebulizer bottom and couples the components together to form the configurable nebulizer. The nebulizer top, nozzle assembly, and nebulizer bottom can be detachably coupled together so that they can easily be separated subsequently by hand or using a tool such as a screwdriver. The nebulizer top, nebulizer bottom, and nozzle assembly can be selected based on their particular properties (e.g., dimensions, features, textures) to optimize the performance of the nebulizer to deliver a nebulized aerosol of medication droplets having a particular size or size range.

In operation 406, a gas supply is connected to a nozzle inlet of the nozzle assembly and a flow of gas, such as air, is supplied to the nebulizer. When the nebulizer is inserted into a patient's mouth and the patient inhales, the combination of the patient's inhalation and the flow of gas from the gas supply through the nozzle assembly creates a sufficient pressure differential to meet the activation pressure. As previously explained, the activation pressure is a pressure differential between the low pressure chamber of the nozzle assembly and the reservoir containing the medicine that is sufficient to draw the medicine upward through a suction line into the low pressure chamber where it mixes with the gas flow passing through the nozzle assembly and nebulizes into an aerosol of medicine droplets. As the medicine droplets are drawn towards the mouthpiece by the patient's inhalation, they can impact an impact surface of the diffuser where the droplets break up into smaller droplets. In operation 408, the patient's inhalation draws the nebulized medicine through the nebulizer mouthpiece and into the patient's mouth and lungs.

Figure 14:
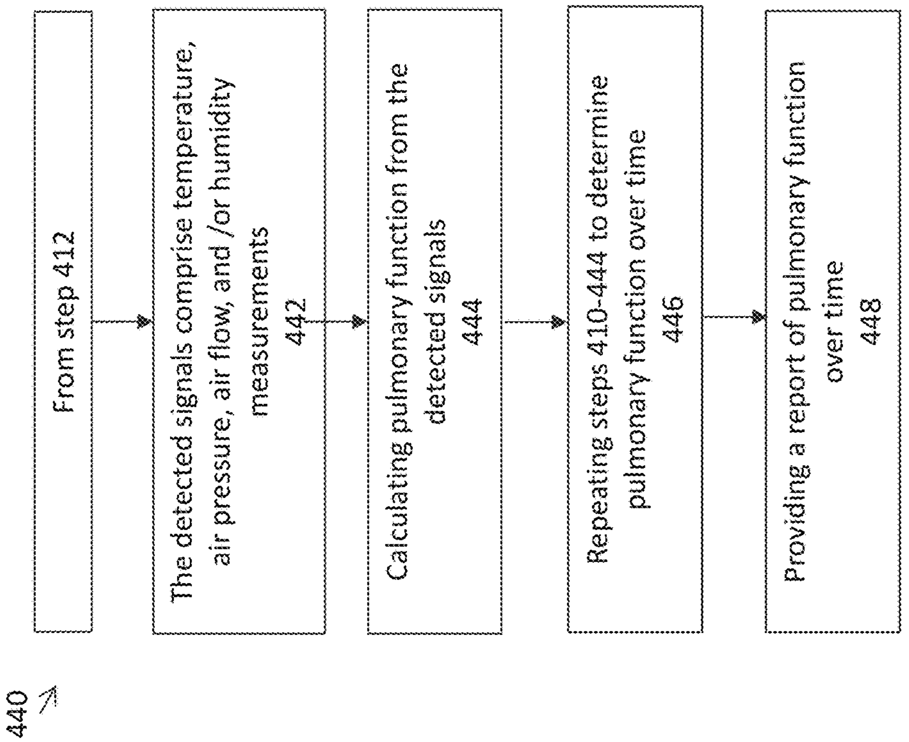
FIG. 14 illustrates a method of determining pulmonary function in accordance with an example embodiment of the disclosure.
Figure 13:
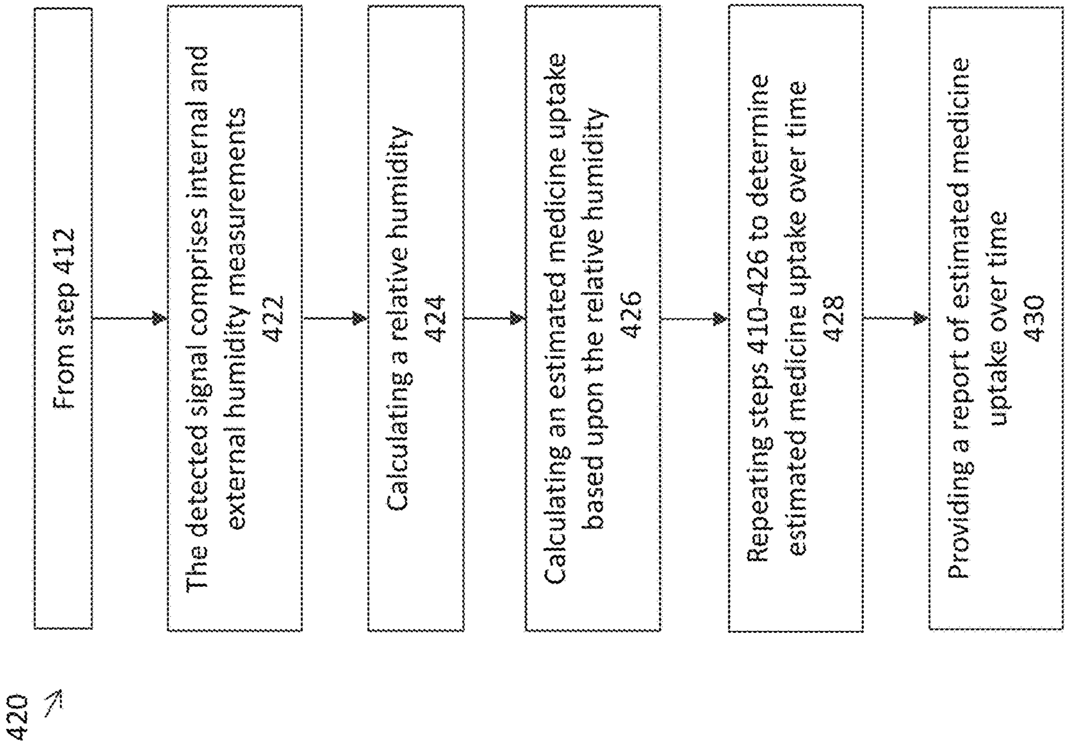
FIG. 13 illustrates a method of estimating medicine uptake in accordance with an example embodiment of the disclosure.
Figure 15:
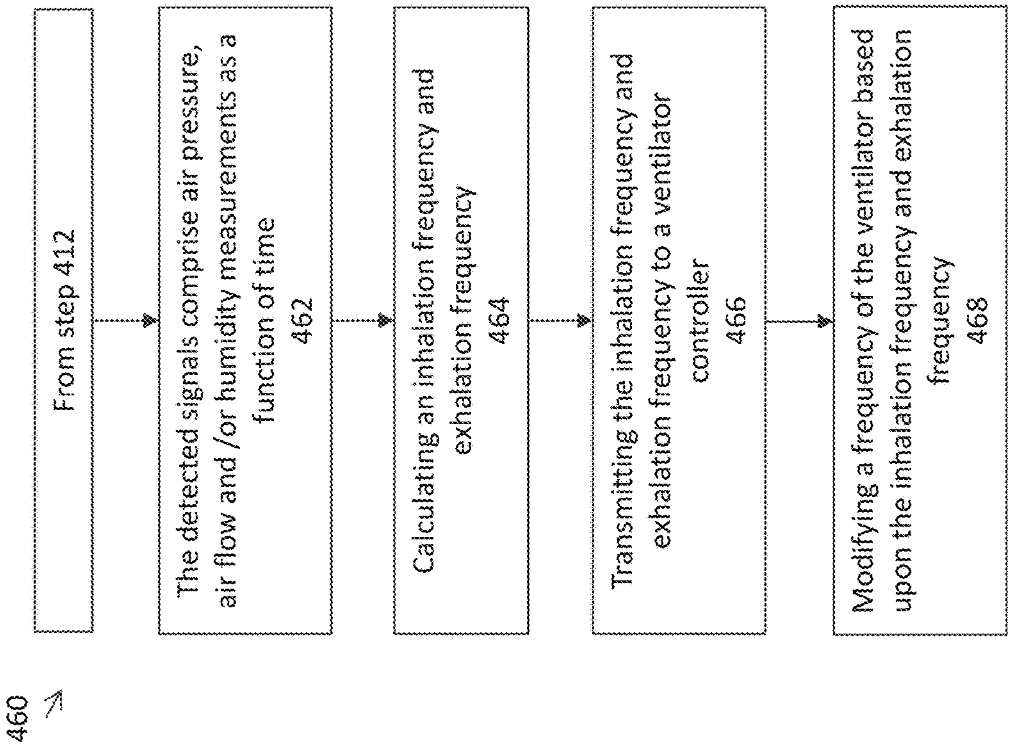
FIG. 15 illustrates a method of using data from a nebulizer for controlling a ventilator in accordance with an example embodiment of the disclosure.

In operation 410, a sensor of the sensor module can detect a signal associated with the nebulizer and collect data associated with the signal. As will be described further in connection with FIGS. 13-17, the sensor and the collected data can relate to a variety of properties, including humidity, temperature, air flow, air pressure, a medication level, or other biometric properties. In operation 412, the sensor provides the collected data to processor where it is analyzed. FIGS. 13, 14, and 15 provide examples of methods for analyzing and using the data collected by the sensor module. The data collected by the one or more sensors of the sensor module can be analyzed for a variety of purposes relating to confirming effective delivery of the medication to the patient and assessing aspects of the patient's health. The methods of FIGS. 13, 14, and 15 are illustrative and it should be understood that the data collected by the sensor module can have a variety of applications.

Referring to FIG. 13, method 420 illustrates an application for humidity data that can be collected by the sensor module. Method 420 highlights that the sensor module can comprise multiple sensors collecting different categories of data. For example, in operation 422, the sensor module comprises an internal humidity sensor that collects humidity measurements from the interior of the nebulizer, as well as an external humidity sensor that collects humidity measurements from the exterior of the nebulizer. Referencing the sensor module 80 of FIG. 4, the external humidity sensor can be located on an outward facing surface of the sensor module 80, whereas the internal humidity sensor can be located on the portion of the sensor module facing the interior of the nebulizer. In operation 424, a processor located within the sensor module can execute instructions and calculate a relative humidity based on the difference between the internal humidity data and the external humidity data. The relative humidity can provide an indication of how much of the medicine has been inhaled by the patient. In operation 426, the processor executes instructions to determine an estimated medicine uptake based on the relative humidity data. In operation 428, the previous operations can be repeated so that relative humidity and an estimated medicine uptake are tracked over time. Lastly, in operation 430, the processor can execute instructions to generate and provide a report of the relative humidity calculations and the estimated medicine uptake over time. Such a report can be useful to a healthcare provider monitoring the levels of medication administered to a patient. As will be described further in connection with FIGS. 16 and 17, the sensor module can include a transmitter that allows for wired or wireless transmission of the collected data and/or any generated reports to a computer such as a handheld tablet or a nearby desktop computer.

Referring now to FIG. 14, method 440 illustrates an application for other types of data that the sensor module can collect. In example method 440, the sensor module comprises a temperature sensor, a humidity sensor, an air pressure sensor, and an air flow sensor. As illustrated in operation 442, the foregoing sensors of the sensor module collect data associated with the patient inhaling from and exhaling into the nebulizer. In operation 444, a processor can receive the data collected from the sensors and execute instructions to analyze the collected data and determine aspects of the patient's pulmonary function, including lung capacity, lung volume, and rates of flow as the patient inhales and exhales. The processor that analyzes the collected data can be a component of the sensor module, or it can be located on another portion of the nebulizer, or it can be a component of an external computing device such as a tablet computer or desktop computer. In operation 446, operations 410, 412, 442 and 444 can be repeated to determine the patient's pulmonary function over time. Lastly, in operation 448, the processor can execute instructions to generate a report of the analysis showing the patient's pulmonary function over time.

Referring now to FIG. 15, method 460 illustrates an application of a nebulizer as a ventilator nebulizer wherein the nebulizer is attached to a ventilator that is assisting a patient with breathing. In operation 462, an air pressure sensor, an air flow sensor, and a humidity sensor of the sensor module can collect data as the patient inhales from and exhales into the ventilator nebulizer. In operation 464, a processor of the sensor module can determine an inhalation frequency and an exhalation frequency of the patient over time by analyzing the data collected in operation 462. In operation 466, the processor can transmit the respiration frequency to a ventilator controller that is controlling the operation of the ventilator. Lastly, in operation 468, the ventilator controller can use the respiration frequency data to modify a frequency of the ventilator as needed to assist the patient with breathing.

Figure 16:
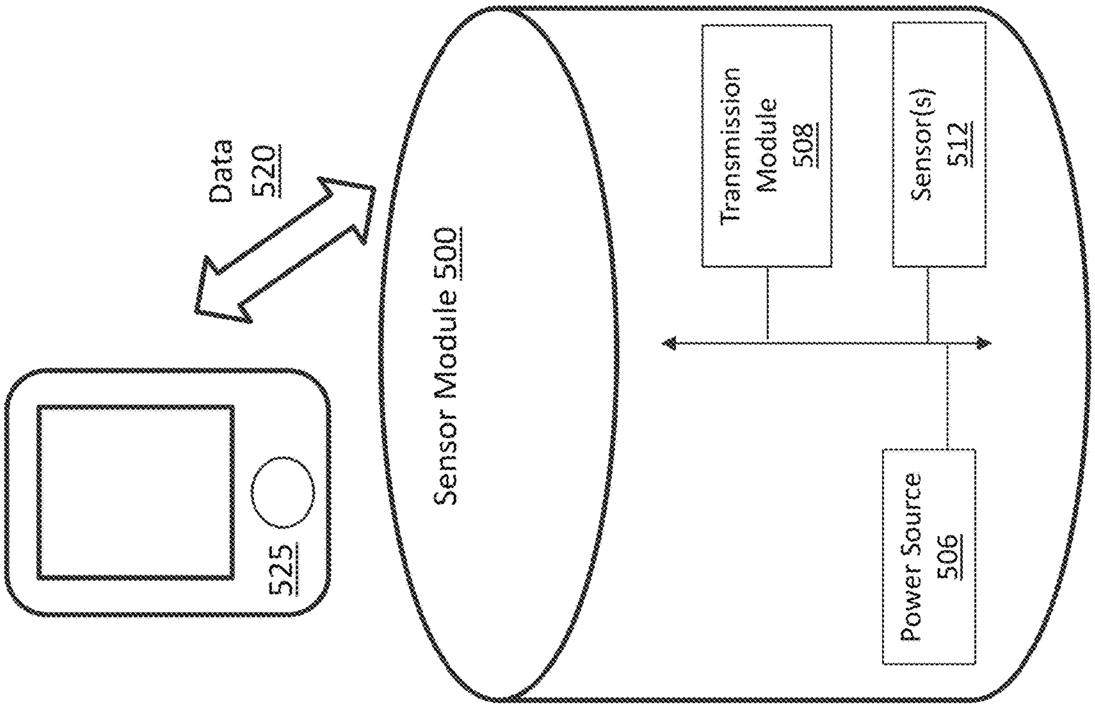
FIGS. 16 and 17 illustrate sensor modules used with nebulizers in accordance with example embodiments of the disclosure.
Figure 17:
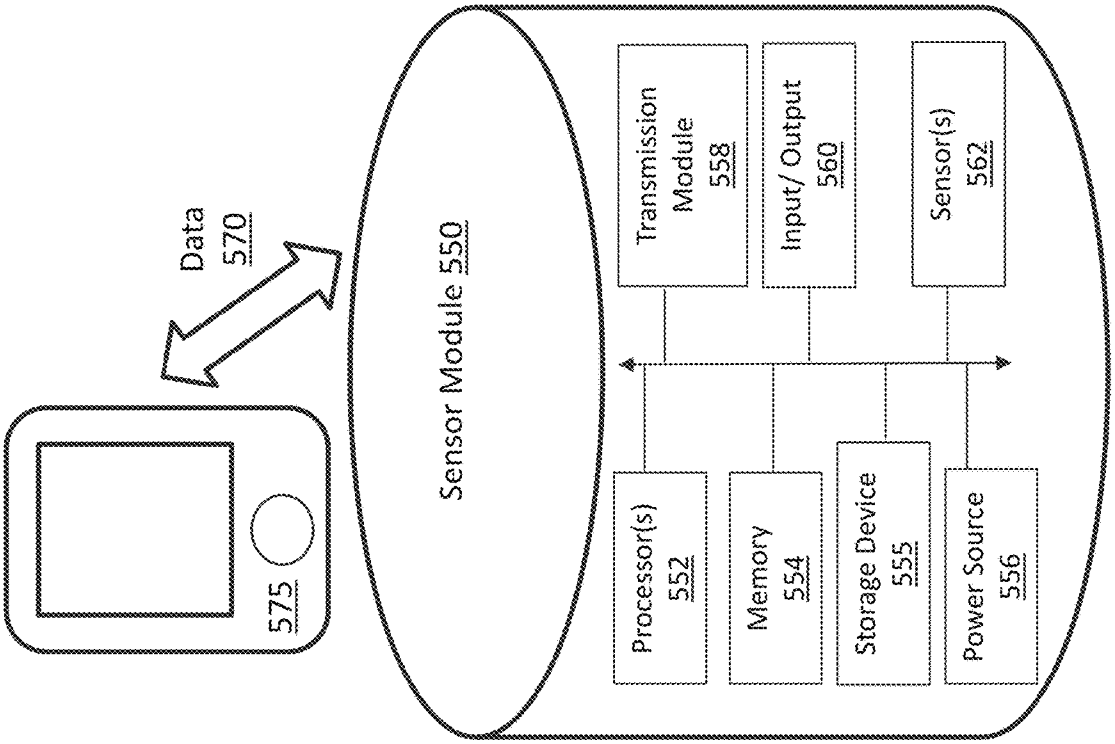

Referring now to FIGS. 16 and 17, examples of sensor modules are illustrated which can be attached to one of the configurable nebulizers as previously described herein. In FIG. 16, sensor module 500 comprises a power source 506, such as a battery, which provides power to the other components of the sensor module 500. Sensor module 500 also includes one or more sensors 512, such as a temperature sensor, a humidity sensor, a pressure sensor, an air flow sensor, a pathogen sensor, an optical biosensor, or a medicine level sensor. As previously referenced, the temperature sensor, the humidity sensor, the pressure sensor, and the air flow sensor can collect data associated with the patient's inhalation from and exhalation into the nebulizer. As additional examples of sensors, a pathogen sensor can analyze the patient's respirations to detect particular bacteria or viruses. An optical biosensor can take a variety of forms and can be configured for one of: fluorescence detection, surface plasmon detection, surface-enhanced Raman scattering detection, colorimetry detection, detection with a fiber Bragg grating, and detection with multimode fiber optics. Lastly, a medicine level sensor can take the form of an optical sensor or an ultrasonic sensor that can measure a level of medicine located in the nebulizer bottom.

One or more of the foregoing sensors can be located at various positions in and on the sensor module so that they are able to collect data from the interior and/or the exterior of the nebulizer. Referring to FIG. 16, sensor module 500 also includes a transmission module 508 that provides wired and/or wireless communication links between the sensor module 500 and external devices. In the example of FIG. 16, an external computing device 525 in the form of a portable tablet is illustrated exchanging data 520 with the sensor module 500 via the communication links provided by the transmission module 508. The data 520 exchanged between the sensor module 500 and the computing device 525 can include the sensor data collected by the sensors 512 as well as control commands sent from the computing device 525 to the sensor module 500.

FIG. 17 illustrates another sensor module that can be attached to a nebulizer and that is more complex than the sensor module of FIG. 16. Similar to sensor module 500, sensor module 550 comprises a power source 556, one or more sensors 562, and a transmission module 558. In addition, sensor module 550 is more complex in that it includes a processor 552, a memory 554, a storage device 555, and an input/output interface 560. The processor 552 can be a hardware processor such as an application specific integrated circuit that executes instructions stored in memory to analyze data collected by the sensors and/or to execute instructions received from an external computer 575. The storage device 555 can be a non-volatile memory that stores the data collected by the sensors 562 as well as instructions for execution by the processor 552. The transmission module 558 can provide wired and/or wireless communication links for exchanging data 570 between the sensor module 550 and external computer 575. Lastly, the input/output interface 560 can take the form of one or more buttons, indicators, or a touch screen allowing control and communication with a user.

Assumptions and Definitions

For any figure shown and described herein, one or more of the components may be omitted, added to another figure, repeated in a figure, and/or substituted with a component from another figure. Accordingly, embodiments shown in a particular figure should not be considered limited to the specific arrangements of components shown in such figure. Further, if a component of a figure is described but not expressly shown or labeled in that figure, the label used for a corresponding component in another figure can be inferred to that component. Conversely, if a component in a figure is labeled but not described, the description for such component can be substantially the same as the description for the corresponding component in another figure.

With respect to the example methods described herein, it should be understood that in alternate embodiments, certain steps of the methods may be performed in a different order, may be performed in parallel, or may be omitted. Moreover, in alternate embodiments additional steps may be added to the example methods described herein. Accordingly, the example methods provided herein should be viewed as illustrative and not limiting of the disclosure.

Referring generally to the examples herein, any components of the nebulizer described herein can be made from a single piece (e.g., as from a mold, injection mold, die cast, 3-D printing process, extrusion process, stamping process, or other prototype methods). In addition, or in the alternative, a component of the apparatus can be made from multiple pieces that are mechanically coupled to each other.

In such a case, the multiple pieces can be mechanically coupled to each other using one or more of a number of coupling methods, including but not limited to epoxy, welding, fastening devices, compression fittings, mating threads, and slotted fittings. One or more pieces that are mechanically coupled to each other can be coupled to each other in one or more of a number of ways, including but not limited to couplings that are fixed, hinged, removeable, slidable, and threaded.

As used herein, "detachably coupled" means components that can be joined together to form a single unit, but that also can be separated by hand or with a tool. Examples of means for detachably coupling the nebulizer components include, but are not limited to snap fit features, compression fittings, interlocking features, magnets, and fasteners such as screws.

As used herein, the term "medication" should be interpreted broadly to include drugs, vaccines, and any other compounds that can be delivered by the nebulizer to a human for medical treatment.

Unless otherwise noted, terms such as "horizontal" and "vertical" are used herein to denote a position when the nebulizer is being used to administer a medication to a patient.

Terms such as "first" and "second" are used merely to distinguish one element (or state of an element) from another. Such terms are not meant to denote a preference and are not meant to limit the embodiments described herein. In the example embodiments described herein, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

The terms "a," "an," and "the" are intended to include plural alternatives, e.g., at least one. The terms "including", "with", and "having", as used herein, are defined as comprising (i.e., open language), unless specified otherwise.

Values, ranges, or features may be expressed herein as "about", from "about" one particular value, and/or to "about" another particular value. When such values, or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In another aspect, use of the term "about" means±20% of the stated value, ±15% of the stated value, ±10% of the stated value, ±5% of the stated value, ±3% of the stated value, or ±1% of the stated value.

Although embodiments described herein are made with reference to examples, it should be appreciated by those skilled in the art that various modifications are well within the scope of this disclosure. Those skilled in the art will appreciate that the example embodiments described herein are not limited to any specifically discussed application and that the embodiments described herein are illustrative and not restrictive. From the description of the example embodiments, equivalents of the elements shown therein will suggest themselves to those skilled in the art, and ways of constructing other embodiments using the present disclosure will suggest themselves to practitioners of the art. Therefore, the scope of the example embodiments is not limited herein.

What is claimed is:

1. A nebulizer comprising:

a nebulizer body, the nebulizer body comprising a nebulizer mouthpiece, a nebulizer top, and a nebulizer bottom, wherein the nebulizer top is configured to detachably couple to the nebulizer bottom;

a nozzle assembly, the nozzle assembly comprising:

a suction line having a suction line inlet, a suction line outlet, and a suction line longitudinal axis passing through the suction line inlet and the suction line outlet;

a nozzle integrally joined to the suction line, the nozzle having a nozzle inlet, a nozzle outlet, and a nozzle longitudinal axis passing through the nozzle inlet and the nozzle outlet, wherein the nozzle longitudinal axis is substantially perpendicular to the suction line longitudinal axis, and wherein the nozzle assembly is configured to detachably couple to the nebulizer body between the nebulizer top and the nebulizer bottom;

a diffuser projecting from an inner surface of the nebulizer top or the nebulizer bottom towards the nozzle assembly, the diffuser comprising an impact surface; and a vent disposed in a top upper wall of the nebulizer top and disposed entirely upstream of the diffuser, the vent providing fluid communication between a low pressure chamber within the nebulizer and an exterior of the nebulizer, thereby decreasing pressure in the low pressure chamber.

2. The nebulizer of claim 1, wherein the nebulizer top comprises:

an upper chamber disposed above the low pressure chamber and disposed adjacent to the mouthpiece, wherein the diffuser is disposed between the low pressure chamber and the upper chamber.

3. The nebulizer of claim 1, wherein the nebulizer top comprises a sensor module attached to an exterior surface of the nebulizer mouthpiece, the sensor module comprising at least one sensor, wherein the at least one sensor is: a temperature sensor, a humidity sensor, a pressure sensor, an air flow sensor, a pathogen sensor, an optical biosensor, or a medicine level sensor.

4. The nebulizer of claim 3, wherein the sensor module is detachably coupled to the nebulizer, and wherein the sensor module further comprises a processor, a storage device that stores data collected by the at least one sensor, and a transmitter that transmits the data to an external computing device.

5. The nebulizer of claim 3, wherein the humidity sensor is an internal humidity sensor that measures an internal humidity within the nebulizer, and wherein the sensor module further comprises an external humidity sensor that measures an external humidity outside the nebulizer.

6. The nebulizer of claim 3, wherein the temperature sensor is configured to measure one of a temperature of the medicine in the nebulizer bottom, a temperature of nebulized medicine, a temperature of air flowing through the mouthpiece, and an ambient temperature.

7. The nebulizer of claim 3, wherein the optical biosensor is configured for one of: fluorescence detection, surface plasmon detection, surface-enhanced Raman scattering detection, colorimetry detection, detection with a fiber Bragg grating, and detection with multimode fiber optics.

8. The nebulizer of claim 3, wherein the sensor module is positioned to collect data relating to a nebulized aerosol of medication exiting the nebulizer mouthpiece and to collect data relating to an exhalation into the nebulizer mouthpiece to determine an uptake of the medicine by a patient.

9. The nebulizer of claim 3, wherein the sensor module is used to determine a pulmonary function of a patient.

10. The nebulizer of claim 7, wherein the sensor module communicates with a ventilator.

11. The nebulizer of claim 1, wherein the nebulizer is a ventilator nebulizer coupled to a ventilator.

12. The nebulizer of claim 1, wherein the nebulizer is a metered dose nebulizer.

13. A method of using a nebulizer, the method comprising:

providing a nebulizer top and a nebulizer bottom, the nebulizer top comprising a vent disposed in a top upper wall of the nebulizer top and disposed entirely upstream of a diffuser projecting from an inner surface of the nebulizer top or the nebulizer bottom;

inserting a nozzle assembly between the nebulizer top and the nebulizer bottom and coupling the nebulizer top to the nebulizer bottom with the nozzle assembly located therebetween;

coupling a gas supply to a nozzle inlet of the nozzle assembly;

providing nebulized medicine that flows from a mouthpiece of the nebulizer;

collecting, with a sensor of a sensor module coupled to the nebulizer, data associated with operation of the nebulizer; and providing the data to a processor that analyzes the data and generates a report associated with the operation of the nebulizer.

14. The method of claim 13, wherein the processor is located within the sensor module and wherein the sensor is at least one sensor, wherein the at least one sensor is: a temperature sensor, a humidity sensor, a pressure sensor, an air flow sensor, a pathogen sensor, an optical biosensor, or a medicine level sensor.

15. The method of claim 14, wherein the humidity sensor is an internal humidity sensor that measures an internal humidity within the nebulizer, and wherein the sensor module further comprises an external humidity sensor that measures an external humidity outside the nebulizer.

16. The method of claim 14, wherein the temperature sensor is configured to measure one of a temperature of the medicine in the nebulizer bottom, a temperature of nebulized medicine, a temperature of air flowing through the mouthpiece, and an ambient temperature.

17. The method of claim 13, wherein the sensor module has a line of sight to a medicine containing reservoir in the nebulizer bottom.

18. The nebulizer of claim 3, wherein the sensor module has a line of sight to a medicine containing reservoir in the nebulizer bottom.

* * * * *